US010273270B2

(12) United States Patent
Yoshida et al.

(10) Patent No.: US 10,273,270 B2
(45) Date of Patent: Apr. 30, 2019

(54) PROTEIN CAPABLE OF BINDING SPECIFICALLY TO IMMUNOGLOBULIN, AND IMMUNOGLOBULIN-BINDING AFFINITY LIGAND

(75) Inventors: Shinichi Yoshida, Takasago (JP); Dai Murata, Takasago (JP); Shunichi Taira, Takasago (JP); Masayuki Takano, Takasago (JP); Keita Iguchi, Takasago (JP); Yoshiyuki Nakano, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 13/636,584

(22) PCT Filed: Mar. 24, 2011

(86) PCT No.: PCT/JP2011/057156
§ 371 (c)(1),
(2), (4) Date: Dec. 21, 2012

(87) PCT Pub. No.: WO2011/118699
PCT Pub. Date: Sep. 29, 2011

(65) Prior Publication Data
US 2013/0096276 A1      Apr. 18, 2013

(30) Foreign Application Priority Data

Mar. 24, 2010   (JP) ................................ 2010-068870

(51) Int. Cl.
| C07K 14/195 | (2006.01) |
| C07K 1/22 | (2006.01) |
| C07K 14/31 | (2006.01) |
| C07K 16/06 | (2006.01) |
| C07K 16/32 | (2006.01) |

(52) U.S. Cl.
CPC .............. *C07K 14/195* (2013.01); *C07K 1/22* (2013.01); *C07K 14/31* (2013.01); *C07K 16/065* (2013.01); *C07K 16/32* (2013.01); *C07K 2317/24* (2013.01); *C07K 2317/55* (2013.01); *C07K 2317/92* (2013.01)

(58) Field of Classification Search
CPC ........ C07K 1/22; C07K 14/195; C07K 14/31; C07K 16/065; C07K 16/32; C07K 2317/24; C07K 2317/55; C07K 2317/92; H01C 17/06; H01R 43/00; H05B 1/00; H05B 2203/008; H05B 2203/016; H05B 3/84
See application file for complete search history.

(56) References Cited

U.S. PATENT DOCUMENTS

| 5,143,844 A | 9/1992 | Abrahmsen et al. |
| 5,525,491 A | 6/1996 | Huston et al. |
| 6,399,750 B1 | 6/2002 | Johansson |
| 6,602,977 B1 | 8/2003 | Ljungqvist et al. |
| 2006/0194950 A1 | 8/2006 | Hober et al. |
| 2009/0299035 A1 | 12/2009 | Iwakura et al. |
| 2010/0048876 A1* | 2/2010 | Hall et al. .................. 530/387.1 |
| 2012/0114686 A1* | 5/2012 | Schneewind .......... C07K 14/31 424/190.1 |

FOREIGN PATENT DOCUMENTS

| CN | 1642976 A | 7/2005 | |
| EP | 1123389 A1 | 8/2001 | |
| EP | 1992692 A1 * | 11/2008 | ............. C12N 15/09 |
| EP | 1992692 A1 | 11/2008 | |
| JP | 2006-304633 A | 11/2006 | |
| JP | 2006304633 A * | 11/2006 | ............. A61K 38/00 |
| JP | 2007-252368 A | 10/2007 | |
| WO | WO-2003/080655 A1 | 10/2003 | |
| WO | WO 03080655 A1 * | 10/2003 | ............. C07K 14/31 |
| WO | WO 2007097361 A1 * | 8/2007 | ............. C12N 15/09 |
| WO | WO-2010/110288 A1 | 9/2010 | |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
On-Line Medical Dictionary definition of Derivative.Nov. 18, 1997.*
Maghnus O'Seaghdha, *Staphylococcus aureus* protein A binding to von Willebrand factor A1 domain is mediated by conserved IgG binding regions, FEBS Journal 273 (2006) 4831-4841.*
The On-line Medical Dictionary, Definition of derivative, accessed on Jul. 7, 2005.*

(Continued)

*Primary Examiner* — Rachael E Bredefeld
*Assistant Examiner* — Erinne R Dabkowski
(74) *Attorney, Agent, or Firm* — Osha Liang LLP

(57) ABSTRACT

An object of the present invention is to create a novel engineered Protein A ligand having better antibody dissociation properties in the acidic condition compared with known engineered Protein A ligands. The present invention provides a protein having an affinity for an immunoglobulin, including an amino acid sequence obtained by introducing, into an amino acid sequence derived from any of E, D, A, B and C domains of Protein A, at least one amino acid substitution at any one or more of amino acid residues corresponding to positions 31 to 37 of the A, B and C domains (positions 29 to 35 of the E domain, positions 34 to 40 of the D domain), which are conserved in all the domains, the protein having a lower affinity for an Fab region of an immunoglobulin than a protein having the amino acid sequence before introduction of the substitution.

18 Claims, 5 Drawing Sheets

Specification includes a Sequence Listing.

(56) References Cited

OTHER PUBLICATIONS

The Sequence Listing for WO2007097361, equivalent to Sequences for EP1992692 A1, accessed on WIPO website, Jan. 20, 2015.*
Protein Data Bank, ID No. 1Q2N, structure of the Z domain of Staphylococcal Protein A, accessed on Aug. 12, 2015.*
Japan Platform for Patent information, English Translation of Detatiled Description for JP2006-304633A, accessed on May 23, 2016.*
Japan Platform for Patent information, English Translation of Claims for JP2006-304633A, accessed on May 23, 2016.*
Japan Platform for Patent information, Sequence Listing for JP2006-304633A, accessed on May 23, 2016.*
Dongmei Zhou, Membrane Affinity Chromatography for Analysis and Purification of Biopolymers, Chromatographia vol. 50, No. 1/2, Jul. 1999.*
Tashiro et al., "Structures of bacterial immunoglobulin-binding domains and their complexes with immunoglobulins", Current Opinion in Structural Biology, 1995, vol. 5, pp. 471-481.
Hober et al., "Protein A chromatography for antibody purification", Journal of Chromatography B, 2007, 848, pp. 40-47.
Jendeberg et al., "Kinetic Analysis of the Interaction Between Protein A Domain Variants and Human Fc Using Plasmon Resonance Detection", Journal of Molecular Recognition, 1995, vol. 8, pp. 270-278.
Low et al., "Future of antibody purification", Journal of Chromatography B, 2007, 848, pp. 48-63.
Roque et al., "Affinity-based methodologies and ligands for antibody purification: Advances and perspectives", Journal of Chromatography A, 2007, vol. 1160, pp. 44-55.
Nilsson et al., "A synthetic IgG-binding domain based on staphylococcal protein A", Protein Engineering, 1987, vol. 1, pp. 107-113.
Jansson et al., "All individual domains of staphylococcal protein a show Fab binding", FEMS Immunology and Medical Microbiology, 1998, vol. 20, pp. 69-78.

Inagawa et al., Separation process engineering, 2008, vol. 38, pp. 201-207.
English translation of International Report on Patentability dated Sep. 25, 2012 in corresponding Application No. PCT/JP2011/057156.
O'Seaghdha et al., "*Staphylococcus aureus* protein A binding to von Willebrand factor A1 domain is mediated by conserved IgG binding regions", FEBS Journal, vol. 273, No. 21, 2006; pp. 4831-4641, XP008152761.
Gomez et al., "*Staphylococcus aureus* Protein A Activates TNFR1 Signaling through Conserved IgG Binding Domains", Journal of Biological Chemistry, vol. 281, No. 29, 2006, pp. 20190-20196, XP055073019.
Cedergren et al., "Mutational analysis of the interaction between staphylococcal protein A and human $IgG_1$", Protein Engineering, vol. 6, No. 4, 1993, pp. 441-448, XP000304302.
Graille et al., "Crystal structure of a *Staphylococcus aureus* protein A domain complexed with the Fab fragment of a human IgM antibody: Structural basis for recognition of B-cell receptors and superantigen activity", Proceedings of the National Academy of Sciences, vol. 97, No. 10, 2000, pp. 5399-5404, XP002284947.
Brown et al., "A Study of the Interactions Between an IgG-Binding Domain Based on the B Domain of Staphylococcal Protein A and Rabbit IgG", Molecular Biotechnology, vol. 10, No. 1, 1998, pp. 9-16, XP055072952.
Yoshida et al., "Rational design and engineering of protein A to obtain the controlled elution profile in monoclonal antibody purification", Chem-Bio Informatics Journal, vol. 12, 2012, pp. 1-13, XP055073094.
Ghose et al., "Antibody Variable Region Interactions with Protein A: Implications for the Development of Generic Purification Processes", Biotechnol. Bioeng., Dec. 20, 2005, 92(6), p. 665-73 (published on line Oct. 4, 2005).
Feldwisch et al., "Design of an Optimized Scaffold for Affibody Molecules", J. Mol. Biol., 2010, vol. 398, No. 2, Apr. 30, 2010, pp. 232-247, XP 027000361.

* cited by examiner

```
         1         10         20        30         40        50
E            AGHDEA------QV-N-----NAD--------------Q-ANV-G--Q----S----
D            ADAQQ------D--S------NM----N--------Q-TNV-G-------ES----
A            ---N-----------------NM---N-----------Q-ANL---------ES----
B            ---------------------N----------------Q-ANL----------------
C            ADNKFNKEQQNAFYEILHLPNLTEEQRNGFIQSLKDDPSVSKEILAEAKKLNDAQAPK
```

SEQ ID Nos: 1-5 correspond to the sequences in Fig 1. Domain E-SEQ ID NO. 1; Domain D-SEQ ID NO. 2; Domain A-SEQ ID NO. 3; Domain B-SEQ ID NO.4; Domain C-SEQ ID NO. 5.

SEQUENCE LISTING

<160> NUMBER OF SEQ ID NOS: 85

<210> SEQ ID NO 1
<211> LENGTH: 56
<212> TYPE: PRT
<213> ORGANISM: Staphylococcus aureus

<400> SEQUENCE: 1

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 6
<211> LENGTH: 56
<212> TYPE: PRT
<213> ORGANISM: Unknown
<220> FEATURE:
<223> OTHER INFORMATION: E-wild mutant

<400> SEQUENCE: 6

Ala Gln His Asp Glu Ala Gln Gln Asn Ala Phe Tyr Gln Val Leu Asn
1               5                   10                  15

Met Pro Asn Leu Asn Ala Asp Gln Arg Asn Ala Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 7
<211> LENGTH: 61
<212> TYPE: PRT
<213> ORGANISM: Unknown
<220> FEATURE:
<223> OTHER INFORMATION: D-wild mutant

<400> SEQUENCE: 7

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Ala
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 8
<211> LENGTH: 58
<212> TYPE: PRT
<213> ORGANISM: Unknown
<220> FEATURE:
<223> OTHER INFORMATION: A-wild mutant

<400> SEQUENCE: 8

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Glu Ser Gln Ala Pro Lys
    50                  55

<210> SEQ ID NO 9
<211> LENGTH: 58
<212> TYPE: PRT
<213> ORGANISM: Unknown
<220> FEATURE:
<223> OTHER INFORMATION: B-wild mutant

<400> SEQUENCE: 9

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Unknown
<220> FEATURE:
<223> OTHER INFORMATION: C-wild mutant

<400> SEQUENCE: 10

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys
    50                  55

<210> SEQ ID NO 11
<211> LENGTH: 290
<212> TYPE: PRT
<213> ORGANISM: Unknown
<220> FEATURE:
<223> OTHER INFORMATION: C-wild mutant

<400> SEQUENCE: 11

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Val Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

```
Thr Glu Glu Gln Arg Asn Val Phe Ile Gln Ser Leu Lys Asp Asp Pro
                 85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
    130                 135                 140

Val Phe Ile Gln Ser Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Val Phe Ile Gln Ser Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Val Phe Ile Gln Ser Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys
    290

<210> SEQ ID NO 12
<211> LENGTH: 881
<212> TYPE: DNA
<213> ORGANISM: Unknown
<220> FEATURE:
<223> OTHER INFORMATION: DNA code

<400> SEQUENCE: 12
ctgcagataa caaatttaac aaagaacaac aaaacgcttt ctacgaaatc ctgcacttgc      60
caaaccttac tgaagaacaa cgtaatgttt tcatccaatc cctgaaagat gatccatctg     120
tatccaaaga aattttggca gaggctaaaa acttaacga cgctcaggcg cctaaggctg     180
ataacaaatt caacaaagaa caacaaaacg cttttatga atccttcac ctgccaaatc      240 ttacagaaga caacgcaac gtattcattc aaagcttgaa ggatgacccct tccgttagca    300 aagagatcct ggctgaagca aaaaagttga atgatgcgca agcaccaaaa gctgataata    360
aattcaacaa agaacaacaa aatgcattct acgaaatctt gcaccttcct aacctgactg    420
aagagcagcg taacgttttt atccagagct gaaagacga tccatctgtc tccaaagaaa    480
ttctcgcaga agcgaagaaa ctgaacgatg ctcaagctcc gaaagcagac aacaaattca    540
ataaggaaca gcaaaacgcg ttttatgaaa ttctgcatct tccaaacttg acagaggaac    600
aacgcaatgt tttcatccaa tccctgaaag atgatccgag cgtttctaag gaaatcttgg    660
ctgaagcaaa aaactgaac gacgctcaag ctccaaaagc ggataacaag tttaacaaag    720
aacaacaaaa tgctttctac gagatcttgc accttccgaa cctgactgaa gaacaacgta    780
acgtatttat tcagtctttg aaggatgacc catccgtaag caaagagatc ctggcagaag    840
```
ctaaaaaatt gaatgatgca caagctccaa ataatctag a            881

<210> SEQ ID NO 13
<211> LENGTH: 172
<212> TYPE: DNA
<213> ORGANISM: Unknown
<220> FEATURE:
<223> OTHER INFORMATION: DNA code

<400> SEQUENCE: 13
ctgcagataa caaatttaac aaagaacaac aaaacgcttt ctacgaaatc ctgcacttgc    60
caaaccttac tgaagaacaa cgtaatgttt tcatccaatc cctgaaagat gatccatctg   120
tatccaaaga aattttggca gaggctaaaa aacttaacga cgctcaggcg cc           172

<210> SEQ ID NO 14
<211> LENGTH: 111
<212> TYPE: DNA
<213> ORGANISM: Unknown
<220> FEATURE:
<223> OTHER INFORMATION: DNA code

<400> SEQUENCE: 14
ggcgcctaag gctgataaca aattcaacaa agaacaacaa aacgcttttt atgaaatcct    60
tcacctgcca aatcttacag aagaacaacg caacgtattc attcaaagct t            111

<210> SEQ ID NO 15
<211> LENGTH: 290
<212> TYPE: DNA
<213> ORGANISM: Unknown
<220> FEATURE:
<223> OTHER INFORMATION: DNA code

<400> SEQUENCE: 15
aagcttgaag gatgacccctt ccgttagcaa agagatcctg gctgaagcaa aaaagttgaa   60
tgatgcgcaa gcaccaaaag ctgataataa attcaacaaa gaacaacaaa atgcattcta   120
cgaaatcttg caccttccta acctgactga agagcagcgt aacgttttta tccagagctt   180
gaaagacgat ccatctgtct ccaaagaaat tctcgcagaa gcgaagaaac tgaacgatgc   240
tcaagctccg aaagcagaca acaaattcaa taaggaacag caaaacgcgt              290

<210> SEQ ID NO 16
<211> LENGTH: 192
<212> TYPE: DNA
<213> ORGANISM: Unknown
<220> FEATURE:
<223> OTHER INFORMATION: DNA code

<400> SEQUENCE: 16
acgcgtttta tgaaattctg catcttccaa acttgacaga ggaacaacgc aatgttttca    60
tccaatccct gaaagatgat ccgagcgttt ctaggaaat cttggctgaa gcaaaaaaac   120
tgaacgacgc tcaagctcca aaagcggata acaagtttaa caaagaacaa caaaatgctt   180
tctacgagat ct                                                       192

<210> SEQ ID NO 17
<211> LENGTH: 140
<212> TYPE: DNA
<213> ORGANISM: Unknown
<220> FEATURE:
<223> OTHER INFORMATION: DNA code

```
<400> SEQUENCE: 17
agatcttgca ccttccgaac ctgactgaag aacaacgtaa cgtatttatt cagtctttga    60
aggatgaccc atccgtaagc aaagagatcc tggcagaagc taaaaaattg aatgatgcac   120
aagctccaaa ataatctaga                                               140

<210> SEQ ID NO 18
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 18
acaacgtaat gctttcatcc aat                                            23

<210> SEQ ID NO 19
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 19
attggatgaa agcattacgt tgt                                            23

<210> SEQ ID NO 20
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 20
acaacgcaac gcattcattc aaa                                            23

<210> SEQ ID NO 21
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 21
tttgaatgaa tgcgttgcgt tgt                                            23

<210> SEQ ID NO 22
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 22
gcagcgtaac gcttttatcc aga                                            23

<210> SEQ ID NO 23
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 23
tctggataaa agcgttacgc tgc                                            23
```

-continued

```
<210> SEQ ID NO 24
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 24
acaacgcaat gctttcatcc aat                                              23

<210> SEQ ID NO 25
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 25
attggatgaa agcattgcgt tgt                                              23

<210> SEQ ID NO 26
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 26
acaacgtaac gcatttattc agt                                              23

<210> SEQ ID NO 27
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 27
actgaataaa tgcgttacgt tgt                                              23

<210> SEQ ID NO 28
<211> LENGTH: 290
<212> TYPE: PRT
<213> ORGANISM: Unknown
<220> FEATURE:
<223> OTHER INFORMATION: C-wild mutant

<400> SEQUENCE: 28

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110
```

```
Gln Ala Pro Lys Ala Asp Asn Lys Phe Asn Lys Glu Gln Gln Asn Ala
        115                 120                 125
Phe Tyr Glu Ile Leu His Leu Pro Asn Leu Thr Glu Glu Gln Arg Asn
        130                 135                 140
Ala Phe Ile Gln Ser Leu Lys Asp Asp Pro Ser Val Ser Lys Glu Ile
145                 150                 155                 160
Leu Ala Glu Ala Lys Lys Leu Asn Asp Ala Gln Ala Pro Lys Ala Asp
                165                 170                 175
Asn Lys Phe Asn Lys Glu Gln Gln Asn Ala Phe Tyr Glu Ile Leu His
            180                 185                 190
Leu Pro Asn Leu Thr Glu Glu Gln Arg Asn Ala Phe Ile Gln Ser Leu
        195                 200                 205
Lys Asp Asp Pro Ser Val Ser Lys Glu Ile Leu Ala Glu Ala Lys Lys
    210                 215                 220
Leu Asn Asp Ala Gln Ala Pro Lys Ala Asp Asn Lys Phe Asn Lys Glu
225                 230                 235                 240
Gln Gln Asn Ala Phe Tyr Glu Ile Leu His Leu Pro Asn Leu Thr Glu
                245                 250                 255
Glu Gln Arg Asn Ala Phe Ile Gln Ser Leu Lys Asp Asp Pro Ser Val
            260                 265                 270
Ser Lys Glu Ile Leu Ala Glu Ala Lys Lys Leu Asn Asp Ala Gln Ala
        275                 280                 285
Pro Lys
    290

<210> SEQ ID NO 29
<211> LENGTH: 873
<212> TYPE: DNA
<213> ORGANISM: Unknown
<220> FEATURE:
<223> OTHER INFORMATION: DNA code

<400> SEQUENCE: 29
gcagataaca aatttaacaa agaacaacaa aacgctttct acgaaatcct gcacttgcca      60
aaccttactg aagaacaacg taatgctttc atccaatccc tgaaagatga tccatctgta     120 tccaagaaa ttttggcaga ggctaaaaaa cttaacgacg ctcaggcgcc taaggctgat      180
aacaaattca caaagaaca acaaaacgct tttatgaaa tccttcacct gccaaatctt       240
acagaagaac aacgcaacgc attcattcaa agcttgaagg atgacccttc cgttagcaaa    300
gagatcctgg ctgaagcaaa aaagttgaat gatgcgcaag caccaaaagc tgataataaa   360
ttcaacaaag aacaacaaaa tgcattctac gaaatcttgc accttcctaa cctgactgaa    420
gagcagcgta acgcttttat ccagagcttg aagacgatc catctgtctc caagaaatt     480 ctcgcagaag cgaagaaact gaacgatgct caagctccga agcagacaa caaattcaat    540 aaggaacagc aaaacgcgtt ttatgaaatt ctgcatcttc caaacttgac agaggaacaa    600
cgcaatgctt tcatccaatc cctgaaagat gatccgagcg tttctaagga atcttggct     660 gaagcaaaaa aactgaacga cgctcaagct ccaaaagcgg ataacaagtt taacaaagaa   720
caacaaaatg ctttctacga gatcttgcac cttccgaacc tgactgaaga acaacgtaac   780
gcatttattc agtctttgaa ggatgaccca tccgtaagca agagatcct ggcagaagct    840 aaaaaattga atgatgcaca agctccaaaa taa                                 873

<210> SEQ ID NO 30
```

```
<211> LENGTH: 24
<212> TYPE: DNA
<213> ORGANISM: Unknown
<220> FEATURE:
<223> OTHER INFORMATION: synthetic oligonucleotide (DNA primer)

<400> SEQUENCE: 30
ctttcatcca agagctgaaa gatg                                           24

<210> SEQ ID NO 31
<211> LENGTH: 24
<212> TYPE: DNA
<213> ORGANISM: Unknown
<220> FEATURE:
<223> OTHER INFORMATION: synthetic oligonucleotide (DNA primer)

<400> SEQUENCE: 31
catctttcag ctcttggatg aaag                                           24

<210> SEQ ID NO 32
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 32
gcattcattc aagagttgaa ggatg                                          25

<210> SEQ ID NO 33
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 33
catccttcaa ctcttgaatg aatgc                                          25

<210> SEQ ID NO 34
<211> LENGTH: 24
<212> TYPE: DNA
<213> ORGANISM: Unknown
<220> FEATURE:
<223> OTHER INFORMATION: synthetic oligonucleotide (DNA primer)

<400> SEQUENCE: 34
cttttatcca ggaattgaaa gacg                                           24

<210> SEQ ID NO 35
<211> LENGTH: 24
<212> TYPE: DNA
<213> ORGANISM: Unknown
<220> FEATURE:
<223> OTHER INFORMATION: synthetic oligonucleotide (DNA primer)

<400> SEQUENCE: 35
cgtctttcaa ttcctggata aaag                                           24

<210> SEQ ID NO 36
<211> LENGTH: 24
<212> TYPE: DNA
<213> ORGANISM: Unknown
<220> FEATURE:
<223> OTHER INFORMATION: synthetic oligonucleotide (DNA primer)

<400> SEQUENCE: 36
```
ctttcatcca agagctgaaa gatg                                          24

<210> SEQ ID NO 37
<211> LENGTH: 24
<212> TYPE: DNA
<213> ORGANISM: Unknown
<220> FEATURE:
<223> OTHER INFORMATION: synthetic oligonucleotide (DNA primer)

<400> SEQUENCE: 37
catctttcag ctcttggatg aaag                                          24

<210> SEQ ID NO 38
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 38
gcatttattc aggagttgaa ggatg                                         25

<210> SEQ ID NO 39
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 39
catccttcaa ctcctgaata aatgc                                         25

<210> SEQ ID NO 40
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 40
caatccctga aaagagatcc atctg                                         25

<210> SEQ ID NO 41
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 41
cagatggatc tcttttcagg gattg                                         25

<210> SEQ ID NO 42
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 42
caaagcttga agagagaccc ttc                                           23

<210> SEQ ID NO 43
<211> LENGTH: 23
<212> TYPE: DNA

```
<213> ORGANISM: Unknown
<220> FEATURE:
<223> OTHER INFORMATION: synthetic oligonucleotide (DNA primer)

<400> SEQUENCE: 43
gaagggtctc tcttcaagct ttg                                              23

<210> SEQ ID NO 44
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 44
gagcttgaaa cgtgatccat ctg                                              23

<210> SEQ ID NO 45
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 45
cagatggatc acgtttcaag ctc                                              23

<210> SEQ ID NO 46
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 46
caatccctga aaagagatcc gag                                              23

<210> SEQ ID NO 47
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 47
ctcggatctc ttttcaggga ttg                                              23

<210> SEQ ID NO 48
<211> LENGTH: 22
<212> TYPE: DNA
<213> ORGANISM: Unknown
<220> FEATURE:
<223> OTHER INFORMATION: synthetic oligonucleotide (DNA primer)

<400> SEQUENCE: 48
gtctttgaag agagacccat cc                                               22

<210> SEQ ID NO 49
<211> LENGTH: 22
<212> TYPE: DNA
<213> ORGANISM: Unknown
<220> FEATURE:
<223> OTHER INFORMATION: synthetic oligonucleotide (DNA primer)

<400> SEQUENCE: 49
ggatgggtct ctcttcaaag ac                                               22
```

<210> SEQ ID NO 50
<211> LENGTH: 34
<212> TYPE: DNA
<213> ORGANISM: Unknown
<220> FEATURE:
<223> OTHER INFORMATION: synthetic oligonucleotide (DNA primer)

<400> SEQUENCE: 50
catccaatcc ctgcgtgatg aaccatctgt atcc                                  34

<210> SEQ ID NO 51
<211> LENGTH: 34
<212> TYPE: DNA
<213> ORGANISM: Unknown
<220> FEATURE:
<223> OTHER INFORMATION: synthetic oligonucleotide (DNA primer)

<400> SEQUENCE: 51
ggatacagat ggttcatcac gcagggattg gatg                                  34

<210> SEQ ID NO 52
<211> LENGTH: 34
<212> TYPE: DNA
<213> ORGANISM: Unknown
<220> FEATURE:
<223> OTHER INFORMATION: synthetic oligonucleotide (DNA primer)

<400> SEQUENCE: 52
cattcaaagc ttgcgcgatg agccttccgt tagc                                  34

<210> SEQ ID NO 53
<211> LENGTH: 34
<212> TYPE: DNA
<213> ORGANISM: Unknown
<220> FEATURE:
<223> OTHER INFORMATION: synthetic oligonucleotide (DNA primer)

<400> SEQUENCE: 53
gctaacggaa ggctcatcgc gcaagctttg aatg                                  34

<210> SEQ ID NO 54
<211> LENGTH: 33
<212> TYPE: DNA
<213> ORGANISM: Unknown
<220> FEATURE:
<223> OTHER INFORMATION: synthetic oligonucleotide (DNA primer)

<400> SEQUENCE: 54
atccagagct tgcgtgacga accatctgtc tcc                                   33

<210> SEQ ID NO 55
<211> LENGTH: 33
<212> TYPE: DNA
<213> ORGANISM: Unknown
<220> FEATURE:
<223> OTHER INFORMATION: synthetic oligonucleotide (DNA primer)

<400> SEQUENCE: 55
ggagacagat ggttcgtcac gcaagctctg gat                                   33

<210> SEQ ID NO 56
<211> LENGTH: 33
<212> TYPE: DNA
<213> ORGANISM: Unknown
<220> FEATURE:

```
<223> OTHER INFORMATION: synthetic oligonucleotide (DNA primer)

<400> SEQUENCE: 56
catccaatcc ctgcgcgatg agccgagcgt ttc                                33

<210> SEQ ID NO 57
<211> LENGTH: 33
<212> TYPE: DNA
<213> ORGANISM: Unknown
<220> FEATURE:
<223> OTHER INFORMATION: synthetic oligonucleotide (DNA primer)

<400> SEQUENCE: 57
gaaacgctcg gctcatcgcg cagggattgg atg                                33

<210> SEQ ID NO 58
<211> LENGTH: 33
<212> TYPE: DNA
<213> ORGANISM: Unknown
<220> FEATURE:
<223> OTHER INFORMATION: synthetic oligonucleotide (DNA primer)

<400> SEQUENCE: 58
attcagtctt tgcgtgatga accatccgta agc                                33

<210> SEQ ID NO 59
<211> LENGTH: 33
<212> TYPE: DNA
<213> ORGANISM: Unknown
<220> FEATURE:
<223> OTHER INFORMATION: synthetic oligonucleotide (DNA primer)

<400> SEQUENCE: 59
gcttacggat ggttcatcac gcaaagactg aat                                33

<210> SEQ ID NO 60
<211> LENGTH: 290
<212> TYPE: PRT
<213> ORGANISM: Unknown
<220> FEATURE:
<223> OTHER INFORMATION: C-wild mutant

<400> SEQUENCE: 60

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Glu Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Glu Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
    130                 135                 140
```

Ala Phe Ile Gln Glu Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Ala Phe Ile Gln Glu Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Ala Phe Ile Gln Glu Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys
    290

<210> SEQ ID NO 61
<211> LENGTH: 873
<212> TYPE: DNA
<213> ORGANISM: Unknown
<220> FEATURE:
<223> OTHER INFORMATION: DNA code

<400> SEQUENCE: 61
gcagataaca aatttaacaa agaacaacaa aacgctttct acgaaatcct gcacttgcca      60
aaccttactg aagaacaacg taatgctttc atccaagagc tgaagatga tccatctgta     120
tccaagaaa ttttggcaga ggctaaaaaa cttaacgacg ctcaggcgcc taaggctgat     180
aacaaattca caaagaaca acaaaacgct ttttatgaaa tccttcacct gccaaatctt     240
acagaagaac aacgcaacgc attcattcaa gagttgaagg atgacccttc cgttagcaaa     300
gagatcctgg ctgaagcaaa aaagttgaat gatgcgcaag caccaaaagc tgataataaa     360
ttcaacaaag aacaacaaaa tgcattctac gaaatcttgc accttcctaa cctgactgaa     420
gagcagcgta acgcttttat ccaggaattg aaagacgatc catctgtctc caagaaatt     480
ctcgcagaag cgaagaaact gaacgatgct aagctccga agcagacaa caaattcaat     540
aaggaacagc aaaacgcgtt ttatgaaatt ctgcatcttc caaacttgac agaggaacaa     600
cgcaatgctt tcatccaaga gctgaaagat gatccgagcg tttctaagga aatcttggct     660
gaagcaaaaa aactgaacga cgctcaagct ccaaaagcgg ataacaagtt taacaaagaa     720
caacaaaatg ctttctacga gatcttgcac cttccgaacc tgactgaaga acaacgtaac     780
gcatttattc aggagttgaa ggatgaccca tccgtaagca agagatcct ggcagaagct     840
aaaaaattga atgatgcaca agctccaaaa taa                                   873

<210> SEQ ID NO 62
<211> LENGTH: 290
<212> TYPE: PRT
<213> ORGANISM: Unknown
<220> FEATURE:
<223> OTHER INFORMATION: C-wild mutant

<400> SEQUENCE: 62

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Arg Asp Pro Ser Val Ser Lys Glu Ile Leu Ala Glu Ala
            35                  40                  45

Lys Lys Leu Asn Asp Ala Gln Ala Pro Lys Ala Asp Asn Lys Phe Asn
50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Lys Arg Asp Pro
                85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
            115                 120                 125

Phe Tyr Glu Ile Leu His Leu Pro Asn Leu Thr Glu Glu Gln Arg Asn
            130                 135                 140

Ala Phe Ile Gln Ser Leu Lys Arg Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Ala Phe Ile Gln Ser Leu
            195                 200                 205

Lys Arg Asp Pro Ser Val Ser Lys Glu Ile Leu Ala Glu Ala Lys Lys
210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Ala Phe Ile Gln Ser Leu Lys Arg Asp Pro Ser Val
            260                 265                 270

Ser Lys Glu Ile Leu Ala Glu Ala Lys Lys Leu Asn Asp Ala Gln Ala
            275                 280                 285

Pro Lys
    290

<210> SEQ ID NO 63
<211> LENGTH: 873
<212> TYPE: DNA
<213> ORGANISM: Unknown
<220> FEATURE:
<223> OTHER INFORMATION: DNA code

<400> SEQUENCE: 63
gcagataaca aatttaacaa agaacaacaa aacgctttct acgaaatcct gcacttgcca      60
aaccttactg aagaacaacg taatgctttc atccaatccc tgaaaagaga tccatctgta     120
tccaaagaaa ttttggcaga ggctaaaaaa cttaacgacg ctcaggcgcc taaggctgat     180
aacaaattca caaagaaca acaaaacgct ttttatgaaa tccttcacct gccaaatctt     240
acagaagaac aacgcaacgc attcattcaa agcttgaaga gacccttc cgttagcaaa      300 gagatcctgg ctgaagcaaa aaagttgaat gatgcgcaag caccaaaagc tgataataaa     360

-continued

```
ttcaacaaag aacaacaaaa tgcattctac gaaatcttgc accttcctaa cctgactgaa    420
gagcagcgta acgcttttat ccagagcttg aaacgtgatc catctgtctc caaagaaatt    480
ctcgcagaag cgaagaaact gaacgatgct caagctccga agcagacaa caaattcaat     540 aaggaacagc aaaacgcgtt ttatgaaatt ctgcatcttc caaacttgac agaggaacaa    600
cgcaatgctt tcatccaatc cctgaaaaga gatccgagcg tttctaagga aatcttggct    660
gaagcaaaaa aactgaacga cgctcaagct ccaaaagcgg ataacaagtt taacaaagaa    720
caacaaaatg ctttctacga gatcttgcac cttccgaacc tgactgaaga caacgtaac    780 gcatttattc agtctttgaa gagagaccca tccgtaagca agagatcct ggcagaagct     840 aaaaaattga atgatgcaca agctccaaaa taa                                 873
```

<210> SEQ ID NO 64
<211> LENGTH: 290
<212> TYPE: PRT
<213> ORGANISM: Unknown
<220> FEATURE:
<223> OTHER INFORMATION: C-wild mutant

<400> SEQUENCE: 64

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Glu Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Glu Pro
                85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Ser Leu Arg Asp Glu Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Ala Phe Ile Gln Ser Leu
        195                 200                 205

Arg Asp Glu Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Ala Phe Ile Gln Ser Leu Arg Asp Glu Pro Ser Val
            260                 265                 270
```

Ser Lys Glu Ile Leu Ala Glu Ala Lys Lys Leu Asn Asp Ala Gln Ala
        275                 280                 285

Pro Lys
    290

<210> SEQ ID NO 65
<211> LENGTH: 873
<212> TYPE: DNA
<213> ORGANISM: Unknown
<220> FEATURE:
<223> OTHER INFORMATION: DNA code

<400> SEQUENCE: 65

| | | | | | | |
|---|---|---|---|---|---|---|
| gcagataaca | aatttaacaa | agaacaacaa | aacgctttct | acgaaatcct | gcacttgcca | 60 |
| aaccttactg | aagaacaacg | taatgctttc | atccaatccc | tgcgtgatga | accatctgta | 120 |
| tccaaagaaa | ttttggcaga | ggctaaaaaa | cttaacgacg | ctcaggcgcc | taaggctgat | 180 |
| aacaaattca | acaagaaca | acaaaacgct | ttttatgaaa | tccttcacct | gccaaatctt | 240 |
| acagaagaac | aacgcaacgc | attcattcaa | agcttgcgcg | atgagccttc | cgttagcaaa | 300 |
| gagatcctgg | ctgaagcaaa | aaagttgaat | gatgcgcaag | caccaaaagc | tgataataaa | 360 |
| ttcaacaaag | aacaacaaaa | tgcattctac | gaaatcttgc | accttcctaa | cctgactgaa | 420 |
| gagcagcgta | acgcttttat | ccagagcttg | cgtgacgaac | catctgtctc | caaagaaatt | 480 |
| ctcgcagaag | cgaagaaact | gaacgatgct | caagctccga | agcagacaa | caaattcaat | 540 |
| aaggaacagc | aaaacgcgtt | ttatgaaatt | ctgcatcttc | caaacttgac | agaggaacaa | 600 |
| cgcaatgctt | tcatccaatc | cctgcgcgat | gagccgagcg | tttctaagga | aatcttggct | 660 |
| gaagcaaaaa | aactgaacga | cgctcaagct | ccaaaagcgg | ataacaagtt | taacaaagaa | 720 |
| caacaaaatg | ctttctacga | gatcttgcac | cttccgaacc | tgactgaaga | caacgtaac | 780 |
| gcatttattc | agtctttgcg | tgatgaacca | tccgtaagca | aagagatcct | ggcagaagct | 840 |
| aaaaaattga | atgatgcaca | agctccaaaa | taa | | | 873 |

<210> SEQ ID NO 66
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 66
ggcgcctact gcagataaca aattc        25

<210> SEQ ID NO 67
<211> LENGTH: 18
<212> TYPE: DNA
<213> ORGANISM: Unknown
<220> FEATURE:
<223> OTHER INFORMATION: synthetic oligonucleotide (DNA primer)

<400> SEQUENCE: 67
tctagattat tttggagc        18

<210> SEQ ID NO 68
<211> LENGTH: 232
<212> TYPE: PRT
<213> ORGANISM: Unknown
<220> FEATURE:
<223> OTHER INFORMATION: C-wild mutant

<400> SEQUENCE: 68

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Glu Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Glu Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
130                 135                 140

Ala Phe Ile Gln Glu Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Ala Phe Ile Gln Glu Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys
225                 230
```

<210> SEQ ID NO 69
<211> LENGTH: 696
<212> TYPE: DNA
<213> ORGANISM: Unknown
<220> FEATURE:
<223> OTHER INFORMATION: DNA code

<400> SEQUENCE: 69

```
gcagataaca aattcaacaa agaacaacaa aacgcttttt atgaaatcct tcacctgcca    60
aatcttacag aagaacaacg caacgcattc attcaagagt tgaaggatga cccttccgtt   120
agcaaagaga tcctggctga agcaaaaaag ttgaatgatg cgcaagcacc aaaagctgat   180
aataaattca caaagaaca acaaaatgca ttctacgaaa tcttgcacct tcctaacctg   240
actgaagagc agcgtaacgc ttttatccag gaattgaaag acgatccatc tgtctccaaa   300
gaaattctcg cagaagcgaa gaaactgaac gatgctcaag ctccgaaagc agacaacaaa   360
ttcaataagg aacagcaaaa cgcgttttat gaaattctgc atcttccaaa cttgacagag   420
gaacaacgca atgctttcat ccaagagctg aaagatgatc cgagcgtttc taaggaaatc   480
ttggctgaag caaaaaaact gaacgacgct caagctccaa aagcggataa caagtttaac   540
aaagaacaac aaaatgcttt ctacgagatc ttgcaccttc cgaacctgac tgaagaacaa   600
cgtaacgcat ttattcagga gttgaaggat gacccatccg taagcaaaga gatcctggca   660
```

```
gaagctaaaa aattgaatga tgcacaagct ccaaaa                               696
```

\<210\> SEQ ID NO 70
\<211\> LENGTH: 174
\<212\> TYPE: DNA
\<213\> ORGANISM: Unknown
\<220\> FEATURE:
\<223\> OTHER INFORMATION: DNA code

\<400\> SEQUENCE: 70

```
gctgacaaca aattcaacaa agaacaacaa aatgctttct atgaaatttt acatttacct     60
aacttaactg aagaacaacg taacgccttc atccaaagcc ttaaagacga tccttcagtg    120
agcaaagaaa ttttagcaga agctaaaaag ctaaacgatg ctcaagcacc aaaa          174
```

\<210\> SEQ ID NO 71
\<211\> LENGTH: 24
\<212\> TYPE: DNA
\<213\> ORGANISM: Unknown
\<220\> FEATURE:
\<223\> OTHER INFORMATION: synthetic oligonucleotide (DNA primer)

\<400\> SEQUENCE: 71

```
ccttcatcca actgcttaaa gacg                                            24
```

\<210\> SEQ ID NO 72
\<211\> LENGTH: 24
\<212\> TYPE: DNA
\<213\> ORGANISM: Unknown
\<220\> FEATURE:
\<223\> OTHER INFORMATION: synthetic oligonucleotide (DNA primer)

\<400\> SEQUENCE: 72

```
cgtctttaag cagttggatg aagg                                            24
```

\<210\> SEQ ID NO 73
\<211\> LENGTH: 24
\<212\> TYPE: DNA
\<213\> ORGANISM: Unknown
\<220\> FEATURE:
\<223\> OTHER INFORMATION: synthetic oligonucleotide (DNA primer)

\<400\> SEQUENCE: 73

```
ccttcatcca aacccttaaa gacg                                            24
```

\<210\> SEQ ID NO 74
\<211\> LENGTH: 24
\<212\> TYPE: DNA
\<213\> ORGANISM: Unknown
\<220\> FEATURE:
\<223\> OTHER INFORMATION: synthetic oligonucleotide (DNA primer)

\<400\> SEQUENCE: 74

```
cgtctttaag ggtttggatg aagg                                            24
```

\<210\> SEQ ID NO 75
\<211\> LENGTH: 25
\<212\> TYPE: DNA
\<213\> ORGANISM: Unknown
\<220\> FEATURE:
\<223\> OTHER INFORMATION: synthetic oligonucleotide (DNA primer)

\<400\> SEQUENCE: 75

```
caaagcctta aaattgatcc ttcag                                           25
```

```
<210> SEQ ID NO 76
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 76
ctgaaggatc aattttaagg ctttg                                   25

<210> SEQ ID NO 77
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 77
caaagcctta acgtgatcc ttcag                                    25

<210> SEQ ID NO 78
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 78
ctgaaggatc acgtttaagg ctttg                                   25

<210> SEQ ID NO 79
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 79
gccttaaaga cgaaccttca gtg                                     23

<210> SEQ ID NO 80
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 80
cactgaaggt tcgtctttaa ggc                                     23

<210> SEQ ID NO 81
<211> LENGTH: 58
<212> TYPE: PRT
<213> ORGANISM: Unknown
<220> FEATURE:
<223> OTHER INFORMATION: C-wild mutant

<400> SEQUENCE: 81

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Leu Leu Lys Asp Asp Pro Ser Val Ser Lys Glu Ile Leu Ala Glu Ala
        35                  40                  45

Lys Lys Leu Asn Asp Ala Gln Ala Pro Lys
```

<210> SEQ ID NO 82
<211> LENGTH: 58
<212> TYPE: PRT
<213> ORGANISM: Unknown
<220> FEATURE:
<223> OTHER INFORMATION: C-wild mutant

<400> SEQUENCE: 82

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Thr Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 83
<211> LENGTH: 58
<212> TYPE: PRT
<213> ORGANISM: Unknown
<220> FEATURE:
<223> OTHER INFORMATION: C-wild mutant

<400> SEQUENCE: 83

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Ile Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 84
<211> LENGTH: 58
<212> TYPE: PRT
<213> ORGANISM: Unknown
<220> FEATURE:
<223> OTHER INFORMATION: C-wild mutant

<400> SEQUENCE: 84

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Arg Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 85
<211> LENGTH: 58
<212> TYPE: PRT
<213> ORGANISM: Unknown
<220> FEATURE:
<223> OTHER INFORMATION: C-wild mutant

<400> SEQUENCE: 85

Ala Asp Asn Lys Phe Asn Lys Glu Gln Gln Asn Ala Phe Tyr Glu Ile

-continued

```
1               5              10              15
Leu His Leu Pro Asn Leu Thr Glu Glu Gln Arg Asn Ala Phe Ile Gln
            20              25              30
Ser Leu Lys Asp Glu Pro Ser Val Ser Lys Glu Ile Leu Ala Glu Ala
        35              40              45
Lys Lys Leu Asn Asp Ala Gln Ala Pro Lys
    50              55
```

PROTEIN CAPABLE OF BINDING SPECIFICALLY TO IMMUNOGLOBULIN, AND IMMUNOGLOBULIN-BINDING AFFINITY LIGAND

CROSS REFERENCE TO RELATED APPLICATIONS

This application is a National Phase filing under 35 U.S.C. § 371 of PCT/JP2011/057156 filed on Mar. 24, 2011; and this application claims priority to Application No. 2010-068870 filed in Japan on Mar. 24, 2010 under 35 U.S.C. § 119; the entire contents of all are hereby incorporated by reference.

TECHNICAL FIELD

The present invention relates to a protein capable of specifically binding to an antibody, an affinity separation matrix containing the protein as an immunoglobulin-binding affinity ligand, and a method for separating and purifying or adsorbing and removing an antibody by the use of the matrix.

BACKGROUND ART

Antibodies specifically bind to substances called antigens, and detoxify and remove antigen-containing factors with the cooperation of other biomolecules and cells. The name "antibody" is particularly based on such an antigen-binding ability, and is also referred to as "immunoglobulin (Ig)" as a chemical name.

Recent developments in genetic engineering, protein engineering, and cell technology have accelerated the development of antibody drugs, which are pharmaceuticals utilizing the abilities of antibodies. Since the antibody drugs more specifically attack a target molecule than conventional pharmaceuticals, use thereof is expected to further reduce side effects and to produce higher therapeutic effects. In fact, these drugs contribute to improvement in various disease conditions.

The quality of antibody drugs is thought to largely depend on the purity compared with the quality of other recombinant protein pharmaceuticals because the doses of these antibody drugs to the body are very large. In order to produce a high purity antibody, techniques using an adsorbing material that contains a ligand molecule capable of specifically binding to an antibody (e.g. affinity chromatography) are commonly employed.

Antibody drugs developed so far are generally monoclonal antibodies. These antibodies are mass produced by recombinant cell-culture technology or the like. The "monoclonal antibodies" refer to antibodies produced by clones of a single antibody-producing cell. Almost all antibody drugs currently available on the market are classified into immunoglobulin G (IgG) subclasses based on their molecular structures. One well-known example of immunoglobulin-binding proteins having affinities for IgG antibodies is Protein A. Protein A is a cell wall protein produced by the gram-positive bacterium *Staphylococcus aureus* and contains a signal sequence S, five immunoglobulin-binding domains (E domain, D domain, A domain, B domain and C domain) and a cell wall-anchoring domain known as XM region (Non Patent Literature 1). In the initial purification step (capturing step) in the process of antibody drug manufacture, affinity chromatography columns where Protein A is immobilized as a ligand on a water-insoluble carrier (hereinafter, referred to as Protein A columns) are commonly used (Non Patent Literatures 1 to 3).

Various techniques for improving the performance of Protein A columns have been developed. Various technological developments in ligands have also been made. Initially, wild-type Protein A has been used as a ligand, but currently, recombinant Protein A altered by protein engineering is used as a ligand in many techniques for improving the column performance.

Typical examples of such recombinant Protein A include recombinant Protein A without the XM region that does not bind to immunoglobulins (rProtein A Sepharose (registered trademark) available from GE health care, Japan). Currently, columns containing as a ligand recombinant Protein A without the XM region are widely used for industrial purposes because these columns have an advantage of suppressing non-specific adsorption of proteins compared with conventional ones.

Also known are inventive techniques in which a recombinant Protein A obtained by introducing a single Cys mutation into Protein A (Patent Literature 1) or a recombinant Protein A obtained by introducing a plurality of Lys mutations (Patent Literature 2) is used as a ligand. These techniques are effective in immobilization of ligands on a water-insoluble carrier and are advantageous in terms of the antibody-binding capacity of columns and for reducing leakage of the immobilized ligands.

Another well-known technique is using, as an engineered recombinant Protein A ligand, an engineered domain obtained by introducing mutation into the B domain (this engineered domain is referred to as Z domain) (Non Patent Literatures 1 and 4 and Patent Literature 3). Specifically, the Z domain is an engineered domain containing a substitution of Ala for Gly at position 29 of the B domain. In the Z domain, a substitution of Val for Ala at position 1 of the B domain is also contained, and this mutation is intended to facilitate genetic engineering preparation of a gene encoding multiple connected domains and does not affect the domain functions (for example, a variant containing a substitution of Ala for Val at position 1 of the Z domain is used in an example of Patent Literature 4).

The Z domain is known to be more alkali resistant than the B domain and has an advantage in reuse of a column through washing with an alkaline solution having high bactericidal and cleansing effect. Patent Literatures 5 and 6 disclose inventive ligands derived from the Z domain, containing a substitution of another amino acid for Asn in order to impart higher alkali resistance, and these ligands are already used for industrial purposes.

As described above, it is widely known that the substitution of Ala for Gly at position 29 of a immunoglobulin-binding domain (E, D, A, B or C domain) of Protein A is a useful mutation strategy. In fact, the prior Protein A engineering technologies developed after the disclosure of the "G29A" mutation in 1987 involve the "G29A" mutation (Patent Literatures 2, 4 and 6).

Another feature of the Z domain is its reduced binding ability to the Fab region of immunoglobulins (Non Patent Literature 5). This feature advantageously facilitates dissociation of an antibody binding to the domain with the use of an acid (Non Patent Literature 1 and Patent Literature 7). If an antibody readily dissociates, an eluate having a higher concentration of antibodies can be recovered using less eluant. Recent developments in antibody drug manufacture have increased the cell culture production capacity beyond 10,000 liters per batch, and in the past few years the antibody expression level has been improved up to nearly 10 g/L (Non Patent Literature 6). These developments have naturally created a need for scale-up of the processing capacity of the downstream purification process, and there is a very large demand for technical improvement in order to recover an eluate having a higher concentration of antibodies by using less eluant.

In addition to the Z domain, engineered Protein A ligands derived from the C domain of Protein A have also been studied (Patent Literature 4). These ligands characteristically take advantage of the inherent high alkali resistance of the wild-type C domain and have been receiving attentions as new alternative base domains to the Z domain prepared based on the B domain. However, our studies on the C domain have revealed a disadvantage that it is difficult to dissociate an antibody binding to the C domain with the use of an acid. The C domain, as taught in Non Patent Literature 2 and Patent Literature 4, has a strong binding ability to the Fab region of immunoglobulins, and this ability is presumed to make it difficult to dissociate the antibody with an acid. In order to overcome this disadvantage, we have examined a C domain variant containing a substitution of Ala for Gly at position 29 for its antibody dissociation properties in the acidic condition. The results have revealed that the antibody tends to more readily dissociate from the domain variant than the wild-type C domain, but its properties are not enough yet.

At present, the "G29A" mutation is the only one mutation which is known to cause an antibody to readily dissociate from the immunoglobulin-binding domains of Protein A, as described above. The "G29A" mutation has the above-mentioned advantages as well as ready dissociation of an antibody, and further technical improvement by mutations at positions other than position 29 is demanded. However, there are so far no reports of mutations at positions other than position 29 which enable readier dissociation of an antibody.

CITATION LIST

Patent Literature

Patent Literature 1: U.S. Pat. No. 6,399,750

Patent Literature 2: JP 2007-252368 A

Patent Literature 3: U.S. Pat. No. 5,143,844

Patent Literature 4: JP 2006-304633 A

Patent Literature 5: European Patent No. 1123389

Patent Literature 6: WO 03/080655

Patent Literature 7: U.S. Publication No. 2006/0194950

Non Patent Literature

Non Patent Literature 1: Hober S. et al., "J. Chromatogr. B", 2007, Vol. 848, pp. 40-47

Non Patent Literature 2: Low D. et al., "J. Chromatogr. B", 2007, Vol. 848, pp. 48-63

Non Patent Literature 3: Roque A. C. A. et al., "J. Chromatogr. A", 2007, Vol. 1160, pp. 44-55

Non Patent Literature 4: Nilsson B. et al., "Protein Engineering", 1987, Vol. 1, pp. 107-113

Non Patent Literature 5: Jansson B. et al., "FEMS Immunology and Medical Microbiology", 1998, Vol. 20, pp. 69-78

Non Patent Literature 6: Jun-ichi Inagawa et al., "Separation process engineering", 2008, Vol. 38, pp. 201-207

SUMMARY OF INVENTION

Technical Problem

An object of the present invention is to create a novel engineered Protein A ligand having better antibody dissociation properties in the acidic condition compared with known engineered Protein A ligands, by introducing mutation(s) at amino acid residue(s) at position(s) other than position 29.

Solution to Problem

The present inventors constructed a large number of recombinant Protein A variant molecules containing amino acid substitutions at positions other than position 29, recovered these variants from transformant cells by protein engineering and genetic engineering techniques, and examined and compared the activities of these variants. Consequently, the present inventors completed the present invention.

Specifically, the present invention relates to a protein having an affinity for an immunoglobulin, including an amino acid sequence obtained by introducing, into an amino acid sequence derived from at least one domain selected from E, D, A, B and C domains of Protein A of SEQ ID Nos:1 to 5, at least one amino acid substitution at any one or more of amino acid residues at positions 31 to 37 of the A, B and C domains, amino acid residues at positions 29 to 35 of the E domain, and amino acid residues at positions 34 to 40 of the D domain, the protein having a lower affinity for an Fab region of an immunoglobulin than a protein before introduction of the substitution.

Preferably, the amino acid sequence derived from at least one domain before introduction of the substitution is any of amino acid sequences of the E, D, A, B and C domains of Protein A of SEQ ID Nos:1 to 5 and amino acid sequences of SEQ ID Nos:6 to 10 derived from the E, D, A, B and C domains of Protein A.

Preferably, the amino acid sequence derived from at least one domain before introduction of the substitution is an amino acid sequence of the C domain of Protein A of SEQ ID No:5 or an amino acid sequence of SEQ ID No: 10 derived from the C domain of Protein A.

Preferably, the domain of the amino acid sequence before introduction of the substitution contains Ser as an amino acid residue corresponding to position 33 of the C domain, Lys as an amino acid residue corresponding to position 35 of the C domain, Asp as an amino acid residue corresponding to position 36 of the C domain, or Asp as an amino acid residue corresponding to position 37 of the C domain.

Preferably, the amino acid substitution to be introduced is a substitution of Glu, Leu or Thr for Ser corresponding to position 33 of the C domain, a substitution of Arg for Lys corresponding to position 35 of the C domain, a substitution of Arg or Ile for Asp corresponding to position 36 of the C domain, or a substitution of Glu for Asp corresponding to position 37 of the C domain.

Preferably, the amino acid substitution to be introduced is a substitution of Glu for Ser corresponding to position 33 of the C domain.

The present invention also relates to a multi-domain protein, including two or more proteins described above, connected together.

The proteins connected together are preferably different from one another, and the number of the proteins connected together is preferably 2 to 5.

The present invention further relates to a DNA encoding any one of these proteins.

Preferably, in the DNA, ligated base sequences each including the domain have a sequence identity of not higher than 90% to one another.

The present invention further relates to a vector containing the DNA.

The present invention further relates to a transformant which is obtainable by transformation of a host with the vector.

Preferably, the host for the transformant is a gram-positive bacterium.

The gram-positive bacterium is preferably a bacterium of *Brevibacillus*, and the bacterium of *Brevibacillus* is more preferably *Brevibacillus choshinensis*.

Further, the present invention relates to a method for producing any one of the proteins, the method including utilizing the transformant or a cell-free protein synthesis system using the DNA.

Preferably, the production method includes: accumulating the protein intracellularly and/or in a periplasmic space of the transformant; and/or secreting the protein extracellularly from the transformant.

Further, the present invention relates to an affinity separation matrix containing: any one of the proteins as an affinity ligand, and a carrier made of a water-insoluble base material on which the protein is immobilized.

The water-insoluble base material preferably includes a synthetic polymer or a polysaccharide, and the polysaccharide is preferably cellulose.

The affinity separation matrix preferably binds to a protein containing an Fc region of an immunoglobulin, and it more preferably binds to an immunoglobulin G or an immunoglobulin G derivative.

Further, the present invention relates to use of the affinity separation matrix for separation of a protein containing an Fc region of an immunoglobulin. Preferably, the separation of a protein containing an Fc region of an immunoglobulin is aimed at separating and recovering a protein consisting only of the Fab region of an immunoglobulin.

Advantageous Effects of Invention

The protein of the present invention has excellent antibody dissociation properties in the acidic condition. Therefore, the use of an affinity separation matrix in which the protein is immobilized on a carrier enables to improve separation and purification of an antibody. Whichever domain is used among the E, D, A, B and C domains, the protein and the affinity separation matrix of the present invention each produce this effect similarly since the protein of the present invention contains mutation(s) at amino acid site(s) conserved in all the domains.

DESCRIPTION OF EMBODIMENTS

Figures 1, 2:
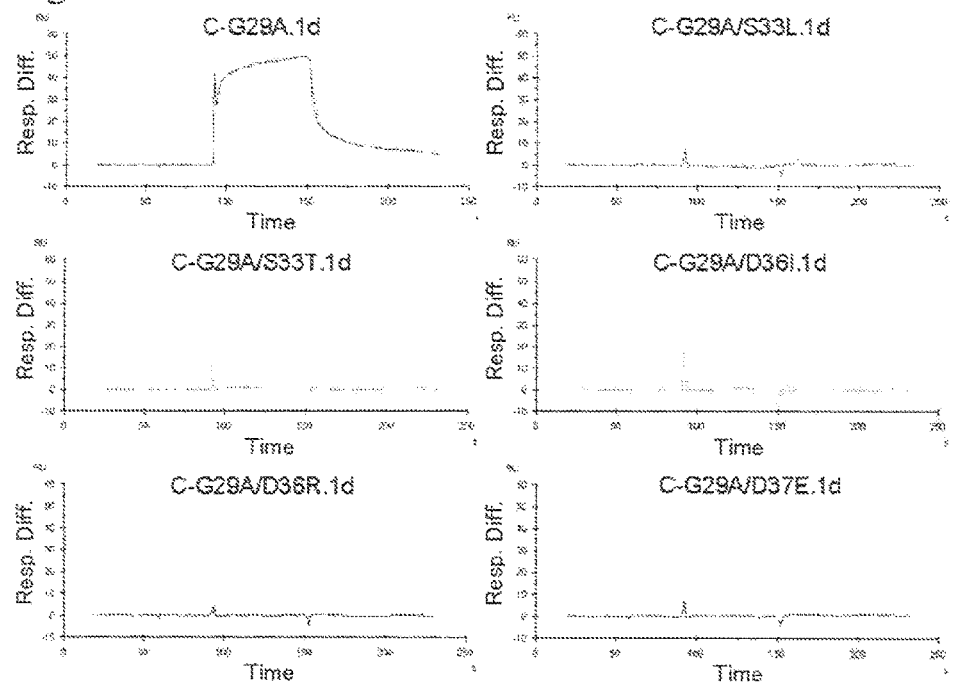
FIG. 1 is a table for comparison of the sequences of E (SEQ ID NO. 1), D (SEQ ID NO. 2), A (SEQ ID NO. 3), B (SEQ ID NO. 4) and C (SEQ ID NO. 5) domains of Protein A of *Staphylococcus* sp., the SEQ ID Nos: 1-5 correspond to the sequences in FIG. 1 (i.e. sequences E, D, A, B and C, respectively)
FIG. 2 are sensorgrams of various GST fused C domain variants binding to a monoclonal IgG-Fab(VH3) by Biacore measurements in Example 10 of the present invention and Comparative Example 3.

The protein of the present invention has an amino acid sequence obtained by introducing, into an amino acid sequence derived from at least one domain selected from E, D, A, B and C domains of Protein A of SEQ ID Nos:1 to 5, at least one amino acid substitution at any one or more of amino acid residues at positions 31 to 37 of the A, B and C domains, amino acid residues at positions 29 to 35 of the E domain, and amino acid residues at positions 34 to 40 of the D domain, which are conserved in all the domains, and the protein also has a lower affinity for the Fab region of an immunoglobulin than a corresponding protein having the amino acid sequence before introduction of the substitution, and has an affinity for an immunoglobulin.

Protein A is a protein containing five connected immunoglobulin-binding domains, i.e., immunoglobulin-binding proteins. The E, D, A, B and C domains of Protein A are immunoglobulin-binding domains having an ability to bind to a region other than complementarity determining regions (CDRs) of immunoglobulins. All the domains are capable of binding to all of the Fc and Fab regions of immunoglobulins and particularly the Fv region in the Fab region. Although the origin of Protein A herein is not particularly limited, Protein A of *Staphylococcus* origin is preferred.

The term "protein" herein is intended to include any molecules of polypeptide structure and therefore include fragmented polypeptide chains and polypeptide chains linked through peptide bonds as well. The term "domain" refers to a higher-order protein structural unit which consists of several tens or hundreds of amino acid residues and is able to fulfill a certain physicochemical or biochemical function.

The amino acid sequence derived from at least one domain means an amino acid sequence before introduction of the mutation. This sequence is not limited only to the wild-type amino acid sequences of the E, D, A, B and C domains of Protein A, and is intended to also include amino acid sequences partially altered by substitution, insertion, deletion and chemical modification of an amino acid residue, provided that they encode proteins having a binding ability to the Fc region. Examples of the amino acid sequence derived from at least one domain include amino acid sequences of the E, D, A, B and C domains of Protein A of *Staphylococcus* origin shown in SEQ ID Nos:1 to 5, and amino acid sequences of the E, D, A, B and C domains of Protein A shown in SEQ ID Nos:6 to 10. Here, the proteins having the amino acid sequences of SEQ ID Nos:6 to 10 are proteins having amino acid sequences obtained by introducing a substitution of Ala for Gly corresponding to position 29 of the C domain into the E, D, A, B and C domains (SEQ ID Nos:1 to 5) of Protein A. Additionally, the Z domain, which is obtained by introducing the A1V and G29A mutations into the B domain, is also encompassed in the amino acid sequence derived from at least one domain because it has a binding ability to the Fc region. Preferred examples of the amino acid sequence before introduction of the mutation include those of domains having high chemical stability and variants thereof.

The protein to which amino acid substitution(s) is/are to be introduced preferably has a sequence identity of not less than 85%, and more preferably not less than 90% to the wild-type amino acid sequence of any of the E, D, A, B and C domains of Protein A, and has an ability to bind to the Fc region.

The amino acid residues conserved in all the domains refer to the same amino acid residues that occur in equivalent locations when the amino acid sequences of the E, D, A, B and C domains are compared. As seen in the sequence comparison table of FIG. 1, the amino acid residues at positions 26 to 39 of the A, B and C domains, positions 24 to 37 of the E domain, and positions 29 to 42 of the D domain are conserved in all the domains. Specific examples of the amino acid residues conserved in all the domains include amino acid residues at positions 31 to 37 of the A, B and C domains, amino acid residues at positions 29 to 35 of the E domain, and amino acid residues at positions 34 to 40 of the D domain. Further, Ser corresponding to position 33 of the C domain, Lys corresponding to position 35 of the C domain, Asp corresponding to position 36 of the C domain, and Asp corresponding to position 37 of the C domain are preferred. In particular, Ser corresponding to position 33 of the C domain is more preferred although the amino acid residues are not limited to these examples. Here, the term "corresponding" means the amino acid residues arranged in the same vertical lines when the E, D, A, B and C domains of Protein A are aligned as shown in FIG. 1.

In general, highly conserved regions of amino acid sequences are important for protein functions in many cases, and a mutation to such a region is likely to cause loss of a protein function. However, although the amino acid sequences of the above-mentioned regions are highly conserved, mutations to these regions do not considerably affect the binding ability to the Fc region of an immunoglobulin while remarkably reducing only the binding ability to the Fab region of an immunoglobulin.

Additionally, it is known that when the amino acid sequence before introduction of the mutation is that of a domain having high chemical stability or a variant thereof, introduction of a new mutation is likely to reduce the chemical stability because the domain consists of as small as about 60 amino acids. For example, a variant containing a substitution of Ala for Phe corresponding to position 30 of the C domain has significantly reduced chemical stability against alkali (Linhult M. et al., PROTEINS: Structure, Function, and Bioinformatics, 2004, Vol. 55, pp. 407-416). However, the amino acid mutations in the present invention can produce the above-mentioned effect while maintaining the inherent chemical stability.

The amino acid substitution means a mutation of deleting an original amino acid and adding a different amino acid at the same position. The different amino acid to be added is not particularly limited and examples thereof include natural proteinogenic amino acids, non-proteinogenic amino acids, and non-natural amino acids. Particularly, from the viewpoint of production by genetic engineering, natural amino acids are suitably used. Examples of natural amino acids include Ala, Phe, Val, Trp, Leu, Pro, Ile, Met, Gly, Asn, Ser, Gln, Thr, Tyr, Cys, Lys, His, Asp, Glu and Arg. Particularly, Glu and Arg are preferred. The number of amino acid substitutions is not particularly limited, provided that the protein containing the substitution(s) has lowered affinity for the Fab region of an immunoglobulin while maintaining its affinity for the entire immunoglobulin. In order to maintain the three-dimensional structure of the protein before introduction of the substitution, the number of substitutions is preferably not more than 4, and more preferably not more than 2.

With respect to the notation of substitutions of amino acid residues, a substitution is represented by an amino acid residue of the wild-type or non-mutated type, followed by the position number of the substitution, followed by an amino acid residue introduced by the substitution. For example, a substitution of Ala for Gly at position 29 is represented by G29A.

Examples of amino acid substitutions at the aforementioned amino acid sites conserved in all the domains include a substitution of Glu, Leu or Thr for Ser corresponding to position 33 of the C domain, a substitution of Arg for Lys corresponding to position 35 of the C domain, a substitution of Arg or Ile for Asp corresponding to position 36 of the C domain, and a substitution of Glu for Asp corresponding to position 37 of the C domain. A particularly preferred one is a substitution of Glu for Ser corresponding to position 33 of the C domain although the substitutions are not limited to these examples.

The protein obtained by introducing the amino acid substitution(s) has a sequence identity of preferably not less than 85%, and more preferably not less than 90% to the wild-type amino acid sequence of any of the E, D, A, B and C domains of Protein A, and has a binding ability to the Fc region.

The protein of the present invention may be a protein consisting only of a single domain containing amino acid substitution(s), or may be a multi-domain protein including two or more of the proteins connected together.

In the case of a multi-domain protein, the proteins connected together may be proteins derived from the same domain (i.e. homopolymer such as homodimer or homotrimer), or proteins derived from different domains (i.e. heteropolymer such as heterodimer or heterotrimer). The number of proteins connected together is preferably 2 or more, more preferably 2 to 10, and still more preferably 2 to 5.

In the multi-domain protein, examples of the connection between monomeric proteins or single domains include, but are not limited to, a connection without any linker amino acid residues and a connection by one or more amino acid residues. The number of amino acid residues used for the connection is not particularly limited. The connection method and the number of connections are also not particularly limited as long as they do not cause destabilization of the three-dimensional structure of the monomeric proteins.

Also included within the scope of the protein of the present invention are fusion proteins in which such a protein or multi-domain protein as described above, as one component, is fused with another protein having a different function. Examples of the fusion proteins include, but are not limited to, fusion proteins with albumin, GST (glutathione S-transferase) or MBP (maltose-binding protein). Proteins expressed in the form of fusion proteins with GST or MBP can be easily purified. Additionally, fusion proteins with a nucleic acid (e.g. DNA aptamer), a drug (e.g. antibiotic substance) or a polymer (e.g. PEG (polyethylene glycol)) are also included within the scope of the protein of the present invention, provided that they produce the same effect of the present invention.

The present invention also relates to a DNA encoding the protein. The DNA may be any DNA having a base sequence which can be translated into the amino acid sequence of the protein of the present invention. Such abase sequence can be obtained by common known techniques, for example, using polymerase chain reaction (hereinafter, abbreviated as PCR) technology. Alternatively, the base sequence can be synthesized by known chemical synthesis techniques or is available from DNA libraries. A codon in the base sequence may be replaced with a degenerate codon, that is, the base sequence is not necessarily the same as the original base sequence, provided that the translated amino acids are the same as those encoded by the original base sequence.

The DNA of the present invention can be obtained by site-directed mutagenesis of a known DNA encoding a wild-type domain of Protein A or a variant thereof. The site-directed mutagenesis can be carried out as follows, using recombinant DNA technology, PCR technology or the like.

In the case of mutagenesis by recombinant DNA technology, for example, if there are suitable restriction enzyme recognition sequences on both sides of a mutagenesis target site in the gene encoding the protein of the present invention, cassette mutagenesis can be used in which a region containing the mutagenesis target site is removed by cleaving these restriction enzyme recognition sites with the restriction enzymes, and then a DNA fragment containing mutation only at the target site, prepared by a method such as chemical synthesis, is inserted.

In the case of site-directed mutagenesis by PCR, for example, double primer mutagenesis can be used in which PCR is carried out using a double-stranded plasmid encoding the protein as a template, and two kinds of synthetic oligo primers containing mutation, complementary to the + and − strands.

In the case of a DNA encoding the multi-domain protein, it can be produced by ligating the desired number of DNAs each encoding the monomeric protein (single domain) of the present invention in tandem. Ligation to produce a DNA encoding the multi-domain protein can be accomplished, for example, by introducing a suitable restriction enzyme site into DNA sequences, fragmenting the DNA sequences with the restriction enzyme, and ligating the obtained double-stranded DNA fragments using a DNA ligase. Only one restriction enzyme recognition site may be introduced or restriction enzyme sites of different types may be introduced. Alternatively, such a DNA encoding the multi-domain protein may be produced, for example, by applying the aforementioned mutagenesis technologies to a DNA encoding Protein A (for example, WO 06/004067). If the base sequences encoding monomeric proteins in the DNA encoding the multi-domain protein are the same, homologous recombination may occur in host cells. Therefore, the ligated DNAs each encoding the monomeric protein preferably have a base sequence identity of not higher than 90%, and more preferably not higher than 85% to one another.

The vector of the present invention contains a base sequence encoding the protein or the multi-domain protein, and a promoter that is operably linked to the base sequence to function in host cells. Typically, the vector can be constructed by linking or inserting the protein-encoding DNA to a vector.

The vector to which the gene is to be inserted is not particularly limited, provided that it is capable of autonomous replication in host cells. As such a vector, a plasmid DNA or a phage DNA can be used. For example, in the case of using *Escherichia coli* host cells, examples of the vector to which the gene is to be inserted include pQE series vectors (QIAGEN), pET series vectors (Merck), and pGEX series vectors (GE health care, Japan). In the case of using *Brevibacillus* host cells, examples of the vector include the known *Bacillus subtilis* vector pUB110, and pHY500 (JP H02-31682 A), pNY700 (JP H04-278091 A), pNU211R2L5 (JP H07-170984 A), and pHT210 (JP H06-133782 A), and the shuttle vector pNCMO2 between *Escherichia coli* and bacteria of *Brevibacillus* (JP 2002-238569 A).

A transformant can be obtained by transformation of a host with the vector. The host is not particularly limited, and preferred examples of those suited for low-cost mass production include *Escherichia coli*, *Bacillus subtilis* and bacteria (eubacteria) of genera including *Brevibacillus*, *Staphylococcus*, *Streptococcus*, *Streptomyces*, and *Corynebacterium*. More preferred are gram-positive bacteria such as *Bacillus subtilis* and bacteria of genera including *Brevibacillus*, *Staphylococcus*, *Streptococcus*, *Streptomyces*, and *Corynebacterium*. Still more preferred are bacteria of *Brevibacillus*, which are known to be used for mass production of Protein A (WO 06/004067).

The bacteria of *Brevibacillus* are not particularly limited and examples thereof include *Brevibacillus agri*, *B. borstelensis*, *B. brevis*, *B. centrosporus*, *B. choshinensis*, *B. formosus*, *B. invocatus*, *B. laterosporus*, *B. limnophilus*, *B. parabrevis*, *B. reuszeri*, and *B. thermoruber*. Preferred examples include *Brevibacillus brevis* 47 (JCM6285), *Brevibacillus brevis* 47K (FERM BP-2308), *Brevibacillus brevis* 47-5Q (JCM8970), *Brevibacillus choshinensis* HPD31 (FERM BP-1087) and *Brevibacillus choshinensis* HPD31-OK (FERM BP-4573). Mutant strains (or derivative strains) such as protease-deficient strains, high-expression strains and sporulation-deficient strains of the bacteria of *Brevibacillus* may be used according to purposes such as improvement in yields. Specifically, the protease mutant strain HPD31-OK of *Brevibacillus choshinensis* (JP H06-296485 A) and the sporulation-deficient strain HPD31-SP3 of *Brevibacillus choshinensis* (WO 05/045005) derived from *Brevibacillus choshinensis* HPD31 may be used.

Examples of the method for transfecting host cells with the vector include, but are not limited to, a method using calcium ions, an electroporation method, a spheroplast method, a lithium acetate method, an *Agrobacterium* infection method, a particle gun method, and a polyethylene glycol method. In order for the obtained gene to express its function in the host cells, for example, a method including incorporation of the gene obtained in the present invention into the genome (chromosome) may be used.

The protein can be produced utilizing the transformant or a cell-free protein synthesis system using the DNA.

In the case of using the transformant for the production of the protein, the transformant may be cultured in a medium to produce and accumulate the protein of the present invention in the cultured cells (including the periplasmic space thereof) or in the culture liquid (extracellularly). Thus, the desired protein can be collected from the culture.

Also in the case of using the transformant for the production of the protein, the protein can be accumulated intracellularly and/or the periplasmic space of the transformant. In the case where the expressed protein is thus intracellularly accumulated, it is advantageous in that the protein can be protected from oxidation, and side reactions with medium components can be avoided. In the case where the expressed protein is accumulated in the periplasmic space, degradation by an intracellular protease can advantageously be inhibited. Alternatively, the protein may be secreted extracellularly from the transformant in the production of the protein. This technique advantageously provides production cost savings because processes such as cell disruption and extraction are not required.

The transformant of the present invention can be cultured in a medium in accordance with a common method for culturing host cells. The medium to be used for culturing the obtained transformant is not particularly limited, provided that it enables high yield production of the protein at high efficiency. Specifically, carbon and nitrogen sources such as glucose, sucrose, glycerol, polypeptone, meat extracts, yeast extracts, and casamino acids can be used. In addition, the medium may be supplemented, as required, with inorganic salts such as potassium salts, sodium salts, phosphates, magnesium salts, manganese salts, zinc salts, and iron salts. In the case of auxotrophic host cells, nutritional substances necessary for their growth may be added to the medium. Moreover, antibiotics such as penicillin, erythromycin, chloramphenicol, and neomycin may be optionally added.

Furthermore, any one or more of a variety of known protease inhibitors such as phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, and ethylenediaminetetraacetic acid (EDTA), and other commercially available protease inhibitors may be added at appropriate concentrations in order to inhibit degradation or molecular-size reduction of the desired protein by a host-derived protease present inside or outside the cells.

In order to assist accurate folding of the protein of the present invention, a molecular chaperone such as GroEL/ES, Hsp70/DnaK, Hsp90 and Hsp104/ClpB may be used. For example, such a molecular chaperone can be coexpressed with the protein of the present invention or can be allowed to coexist with the protein of the present invention by combining into a fusion protein or the like. Further examples of techniques for accurate folding of the protein of the present invention include, but are not limited to, addition of an additive for assisting accurate folding to the medium; and culturing at low temperatures.

Examples of media for culturing transformant cells obtained from an *Escherichia coli* host include LB medium (1% triptone, 0.5% yeast extract, 1% NaCl) and 2xYT medium (1.6% triptone, 1.0% yeast extract, 0.5% NaCl).

Examples of media for culturing transformant cells obtained from a *Brevibacillus* host include TM medium (10 peptone, 0.5% meat extract, 0.2% yeast extract, 1% glucose, pH 7.0) and 2SL medium (4% peptone, 0.5% yeast extract, 2% glucose, pH 7.2).

The protein of the present invention is accumulated in the cultured cells (including the periplasmic space thereof) or in the culture liquid (extracellularly) by aerobically culturing the cells at a temperature of 15° C. to 42° C., preferably 20° C. to 37° C., for several hours to several days in an aeration-stirring condition prior to recovery. In some cases, the cells may be cultured anaerobically without aeration.

In the case where the recombinant protein is produced and secreted, the produced recombinant protein can be recovered, after culturing the cells, by separating the cultured cells from the supernatant containing the secreted protein by a common separation method such as centrifugation and filtration.

Also in the case where the protein is accumulated in the cultured cells (including the periplasmic space), the protein produced and accumulated in the cells can be recovered, for example, by collecting the cells from the culture liquid by centrifugation, filtration or the like, and then disrupting the cells by sonication, a French press treatment or the like, and/or adding an agent for making the protein soluble, such as a surfactant.

In the case where the protein of the present invention is produced by a cell-free protein synthesis system, the cell-free protein synthesis system is not particularly limited, and examples thereof include synthesis systems derived from procaryotes, plant cells, and higher animal cells.

Purification of the protein of the present invention can be accomplished by any one or an appropriate combination of techniques such as affinity chromatography, cation or anion exchange chromatography and gel filtration chromatography.

Examples of techniques to confirm whether the obtained purified product is the desired protein include common techniques such as SDS polyacrylamide gel electrophoresis, N-terminal amino acid sequence analysis and Western blot analysis.

An affinity separation matrix can be prepared by immobilizing as an affinity ligand the protein produced by the above method on a carrier made of a water-insoluble base material. The term "affinity ligand" refers to a substance (functional group) that selectively captures (binds to) a target molecule in a mixture of molecules due to a specific affinity between molecules, typically, antigen-antibody binding affinity, and refers herein to a protein that specifically binds to an immunoglobulin. The term "ligand" as used alone herein is synonymous with the "affinity ligand".

Examples of the carrier made of a water-insoluble base material used in the present invention include inorganic carriers such as glass beads and silica gel; organic carriers such as synthetic polymers (e.g. cross-linked polyvinyl alcohol, cross-linked polyacrylate, cross-linked polyacrylamide, cross-linked polystyrene) and polysaccharides (e.g. crystalline cellulose, cross-linked cellulose, cross-linked agarose, cross-linked dextran); and composite carriers of combinations of these carriers such as organic-organic or organic-inorganic composite carriers.

Examples of commercial products thereof include GCL2000 (porous cellulose gel), Sephacryl S-1000 (prepared by covalently cross-linking allyl dextran with methylenebisacrylamide), Toyopearl (methacrylate carrier), Sepharose CL4B (cross-linked agarose carrier) and Cellufine (cross-linked cellulose carrier). It should be noted that the water-insoluble carrier usable in the present invention is not limited only to the carriers listed above.

In view of the purpose and method of usage of the affinity separation matrix, the water-insoluble carrier used in the present invention desirably has a large surface area and is preferably a porous matrix having a large number of fine pores of a suitable size. The carrier may be in any form such as beads, monolith, fiber, or film (including hollow fiber), and any form can be selected appropriately.

Immobilization of the ligand on the carrier may be accomplished, for example, by a conventional coupling method utilizing an amino, carboxyl or thiol group of the ligand. Examples of such a coupling method include immobilization methods including activation of the carrier by reacting the carrier with cyanogen bromide, epichlorohydrin, diglycidyl ether, tosyl chloride, tresyl chloride, hydrazine, sodium periodate, or the like (or introduction of a reactive functional group into the carrier surface), followed by a coupling reaction between the carrier and a compound to be immobilized as the ligand; and immobilization methods involving condensation and crosslinking by adding a condensation reagent such as carbodiimide or a reagent containing a plurality of functional groups in the molecule, such as glutaraldehyde, to a system containing the carrier and a compound to be immobilized as the ligand.

A spacer molecule consisting of a plurality of atoms may also be introduced between the ligand and the carrier, or alternatively, the ligand may be directly immobilized on the carrier. That is, for immobilization, the protein of the present invention may be chemically modified, or may incorporate an additional amino acid residue useful for immobilization. Examples of amino acids useful for immobilization include amino acids containing, in a side chain, a functional group useful for a chemical reaction for immobilization, and specifically include Lys which contains an amino group in a side chain, and Cys which contains a thiol group in a side chain. In the nature of the present invention, the matrix containing the protein of the present invention as a ligand immobilized therein should also have the effect of the protein of the present invention, and the matrix is also included within the scope of the present invention even if the protein is modified or altered in any manner for immobilization.

The affinity separation matrix is thus obtained by immobilizing the protein of the present invention. Therefore, due to the activity of the protein of the present invention, per se, the affinity separation matrix is capable of binding to a protein containing the Fc region of an immunoglobulin. Accordingly, the protein containing the Fc region of an immunoglobulin can be separated and purified by an affinity column chromatography purification method using the protein and the affinity separation matrix of the present invention. The term "protein containing the Fc region of an immunoglobulin" refers to a protein containing any part of the Fc region to which Protein A binds. It should be noted that the protein is not required to contain the entire Fc region as long as Protein A can binds thereto.

Examples of the protein containing the Fc region of an immunoglobulin include, but are not limited to, immunoglobulin Gs and immunoglobulin G derivatives. Specific examples of the protein containing the Fc region of an immunoglobulin include IgG of the VH3 subfamily, in particular, human IgG of the VH3 subfamily (monoclonal antibody). The protein and the affinity separation matrix of the present invention preferably have a lower affinity for the Fab region of IgG of the VH3 subfamily than a protein before introduction of the mutation, and at the same time they preferably have an affinity for the Fc region of IgG subtypes 1, 2 and 4. Nearly half of human VH germ line genes belong to the VH3 subfamily. In fact, pharmaceuticals containing IgG antibodies of the VH3 subfamily are under study and some of them are already commercially available. In addition, it is regarded as a known fact that in the case of using a ligand maintaining the binding ability to the Fab region of an immunoglobulin of the VH3 subfamily in an affinity separation matrix for antibody purification, the remaining binding ability adversely affects the dissociation properties of the antibody in the acidic condition, from some literatures (Ghose S. et al., Biotechnology and bioengineering, 2005, vol. 92, No. 6). Therefore, the protein and the affinity separation matrix of the present invention preferably have a reduced binding ability to the Fab region of human IgG of the VH3 subfamily.

The term "immunoglobulin G derivatives" is a generic name of altered synthetic proteins to which Protein A binds, such as chimeric immunoglobulin Gs in which domain(s) of human IgG is/are partially replaced and fused with IgG domain(s) of another species, humanized immunoglobulin Gs in which CDRs (Complementarity Determining Regions) of human IgG are replaced and fused with antibody CDRs of another species, immunoglobulin Gs whose Fc region has a molecularly altered sugar chain, and artificial immunoglobulin Gs in which the Fv region and the Fc region of human IgG are fused.

The regions to be bound are loosely defined as "Fab region (in particular, Fv region)" and "Fc region", and the protein to which the protein and the affinity separation matrix of the present invention bind may be one obtained by further altering (e.g. fragmenting) the Fab or Fc region while maintaining the three-dimensional structure of the region to which Protein A binds by protein engineering techniques based on the three-dimensional structure of the antibody, which is already known.

Purification of the protein containing the Fc region of an immunoglobulin using an affinity column filled with the affinity separation matrix of the present invention is accomplished in accordance with an affinity column chromatography purification method using a Protein A column which is already on the market (Non Patent Literature 3). Specifically, a buffer containing the protein containing the Fc region of an immunoglobulin is neutralized and the resulting solution is allowed to pass through the affinity column filled with the affinity separation matrix of the present invention so that the protein containing the Fc region of an immunoglobulin is adsorbed on the affinity separation matrix. Next, an adequate amount of a pure buffer is allowed to pass through the affinity column to wash the inside of the column. At this time, the desired protein containing the Fc region of an immunoglobulin remains adsorbed on the affinity separation matrix of the present invention in the column. Subsequently, an acidic buffer adjusted to an adequate pH (which may contain a substance for accelerating dissociation of the protein from the matrix) is allowed to pass through the column to elute the desired protein containing the Fc region of an immunoglobulin. Thus, high-level purification can be achieved.

The affinity separation matrix of the present invention can be reused through a washing process in which a pure buffer (in some cases, a solution containing an appropriate modifier or organic solvent) having an adequately strong acidity or alkalinity which does not completely impair the functions of the ligand compound and the carrier base material is allowed to pass through the matrix.

An advantageous effect of the protein of the present invention and the affinity separation matrix utilizing this protein is that they have an affinity for an immunoglobulin but have a reduced affinity for the Fab region of the immunoglobulin. In general, the domains of Protein A more strongly bind to the Fc region than to the Fab (Fv) region (Non Patent Literature 3). Thus, the "affinity for an immunoglobulin" of Protein A and the domains essentially refers to the affinity for the Fc region, and the degree of affinity for an immunoglobulin does not largely change when only the strength of binding to the Fab region is changed. The protein of the present invention shows a reduction in the secondary affinity for the Fab region which the immunoglobulin-binding domains of Protein A inherently have. Therefore, the protein of the present invention has an advantageous effect of eliminating an influence of the secondary binding by interaction with an immunoglobulin. On the other hand, the affinity for the Fc region is maintained, and therefore the affinity for the immunoglobulin as a whole is maintained. When the affinity of the protein of the present invention for an immunoglobulin is evaluated as an affinity for a human immunoglobulin G drug by a Biacore system described below, the affinity constant (KA) is preferably $10^6$ ($M^{-1}$) or higher, and more preferably $10^7$ ($M^{-1}$) or higher.

The affinity of the protein and the affinity separation matrix of the present invention for a protein containing the Fc region of an immunoglobulin can be tested by for example, but not limited to, a biosensor such as a Biacore system (GE health care, Japan) based on the surface plasmon resonance principle.

The measurement conditions may be determined such that a binding signal emitted when Protein A binds to the Fc region of an immunoglobulin can be detected. Specifically, the affinity can be easily evaluated by measurement at a temperature of 20° C. to 40° C. (constant temperature) and a neutral pH of 6 to 8.

The immunoglobulin molecule as a binding partner is not particularly limited, provided that it allows detection of binding to the Fab region. However, fragmented immunoglobulin molecules (Fab fragments, Fv fragments) obtained by separating the Fab region from the Fc region are preferred because binding to the Fc region is also detected if an immunoglobulin molecule containing the Fc region is used. Further, more preferred are Fab fragments of immunoglobulins of the VH3 subfamily, which are already known to allow Protein A to bond to the Fab region.

Those skilled in the art can easily determine the difference in affinity by obtaining sensorgrams of the binding reactions with the same immunoglobulin molecule under the same measurement conditions, and making a comparison between binding parameters obtained by the analysis of proteins before and after introduction of a mutation. Here, the sequences to be compared for the difference in affinity should be the same except for the mutated site. For example, when the sequences of the B domain and a C domain variant containing the D36R mutation are used for evaluation of the effect of the D36R mutation, as the amino acid sequence of a protein before introduction of the mutation and the amino acid sequence of a protein after introduction of the mutation, respectively, the comparison between them does not make sense.

Examples of binding parameters include the affinity constant (KA) and the dissociation constant (KD) (Nagata et al., "Real-time analysis of biomolecular interactions", Springer-Verlag Tokyo, 1998, p. 41). The affinity constants of domain variants of the present invention for Fab can be determined with a Biacore system by adding each domain variant to a flow channel in an experimental system that includes a sensor chip with an Fab fragment of an immunoglobulin of the VH3 subfamily immobilized thereon, at a temperature of 25° C. and a pH of 7.4. Among proteins having mutated sequences according to the present invention, those having an affinity constant (KA) reduced to not higher than ½ of the affinity constant of a protein having a sequence before introduction of the mutation are suitably used. The affinity constant (KA) is more preferably reduced to not higher than ⅕, and still more preferably not higher than ¹⁄₁₀. Here, it should be noted that although the affinity constant is also described as the association constant in some literatures, these two terms basically mean the same.

In general, C domain variants containing a substitution of Ala for Gly at position 29 have a KA for Fab of $1\times10^4$ to $1\times10^5$ $(M^{-1})$. C domain variants containing mutation(s) according to the present invention in addition to the substitution of Ala for Gly at position 29 and having a KA reduced to lower than $1\times10^4$ $(M^{-1})$ are suitably used in the present invention. More suitably used are variants having a KA of $0.5\times10^4$ $(M^{-1})$ or lower. The Fab used in the KA measurement may be obtained by fragmenting an immunoglobulin G into an Fab fragment and an Fc fragment by papain; or may be prepared using a genetically engineered production system that expresses only the Fab region of an immunoglobulin G.

Because of its reduced binding ability to the Fab region of an immunoglobulin, the affinity separation matrix of the present invention excellently dissociates an antibody in the process of eluting the antibody with an acidic solution. Specifically, since the affinity separation matrix of the present invention allows elution under acidic elution conditions closer to neutral, damage to an antibody caused under acidic conditions can advantageously be suppressed. The acidic elution conditions closer to neutral specifically mean conditions with a pH of about 3.0 to 5.0 compared with the pH range of common acidic elution conditions of about 2.0 to 3.5. Elution under the conditions reduces damage to an antibody (Ghose S. et al., Biotechnology and bioengineering, 2005, vol. 92, No. 6). The excellent antibody dissociation properties in the acidic condition mean, for example, dissociation under acidic elution conditions closer to neutral, or a sharper elution peak profile obtained when an antibody is eluted under acidic conditions. A sharper elution peak profile in chromatography indicates that an eluate having a higher concentration of antibodies can be recovered using less eluant.

Additionally, the affinity separation matrix of the present invention enables the Fab region to be separated and recovered readily as a flow through fraction from a mixture of a molecule containing the Fc region and a molecule containing only the Fab region.

EXAMPLES

The following description is offered to illustrate in more detail the present invention based on examples, but the scope of the present invention is not limited to these examples.

Proteins obtained in examples are each represented by "an alphabet indicating a domain—an introduced mutation (wild for the wild-type)". For example, the wild-type C domain of Protein A is represented by "C-wild", and a C domain variant containing the G29A mutation is represented by "C-G29A". A domain variant containing two mutations together is represented by indicating the two mutations together with a slash. For example, a C domain variant containing the G29A and S33E mutations is represented by "C-G29A/S33E". A protein containing a plurality of single domains connected is represented together with a period (.) and the number of connected domains with "d". For example, a protein consisting of five connected C domain variants containing the G29A and S33E mutations is represented by "C-G29A/S33E.5d".

[Example 1] Preparation of DNA Encoding C-G29A. 5d

A base sequence encoding a protein consisting of five connected C-G29Vs was constructed by reverse translation from the amino acid sequence (C-G29V.5d, SEQ ID No: 11) of the protein. Codons were assigned such that the codon usage frequency of the protein was closer to the codon usage frequency of the cell surface protein HWP, which is expressed in a large amount in *Brevibacillus choshinensis* HPD31 (Ebisu S., "J. Bacteriol.", 1990, No. 172, pp. 1312-1320), and that the sequence identity between the base sequences of the five domains was low. The restriction enzyme recognition sites for PstI and XbaI were also prepared on the 5' side and 3' side, respectively, of the sequence encoding the five connected domains. The prepared DNA fragment was commissioned from Takara Bio Inc. The sequence of the prepared DNA fragment is shown as SEQ ID No:12.

The prepared DNA fragment encoding C-G29V.5d was digested with PstI and XbaI (both available from Takara Bio Inc.), and then separated and purified by agarose gel electrophoresis. Separately, the plasmid vector pNK3262 for *Brevibacillus* was digested with PstI and XbaI, and then purified and recovered. The recovered vector was treated with alkaline phosphatase (Takara Bio Inc.) for dephosphorylation. Both were mixed and ligated with Ligation High (TOYOBO CO., LTD.). In this manner, a plasmid vector pNK3262-C-G29V.5d capable of expressing C-G29V.5d was constructed. *Brevibacillus choshinensis* FY-1 was transformed using the plasmid vector obtained by the above procedures. The transformation was accomplished by a known electroporation method ("Biosci. Biotech. Biochem.", 1997, No. 61, pp. 202-203). The *Brevibacillus choshinensis* FY-1 is a Phe- and Tyr-requiring strain obtained by mutating *Brevibacillus choshinensis* HPD31-OK (JP H06-296485 A).

The gene encoding C-G29V.5d in the plasmid pNK3262-C-G29V.5d thus prepared was cleaved into five DNA fragments so that each fragment contained a codon for Val-29 of the individual domain. The domains were numbered 1 to 5 starting from the N-terminal side. The DNA fragment for the domain 1 was digested with PstI and NarI; the DNA fragment for the domain 2 was digested with Nan and HindIII; the DNA fragment for the domain 3 was digested with HindIII and MluI; the DNA fragment for the domain 4 was digested with MluI and BglII; and the DNA fragment for the domain 5 was digested with BglII and XbaI (NarI is available from TOYOBO CO., LTD. and the others are available from Takara Bio Inc.), each followed by separation and purification using an agarose gel to give the respective DNA fragments.

Two cloning vectors pSL301 (Invitrogen) and pUC19 (Takara Bio Inc.) were digested with the same pairs of restriction enzymes as those used for the DNA fragments encoding the domains. The resulting fragments were each mixed with the corresponding DNA fragment, and they were ligated with Ligation High. In this manner, plasmids each containing one of the five-divided DNA fragments were constructed. The plasmids are represented in correspondence to the domain numbers as pUC19-V29-d1, pUC19-V29-d2, pSL301-V29-d3, pSL301-V29-d4, and pSL301-V29-d5. The sequences (including the restriction enzyme recognition sites) of the DNA fragments of the C-G29V.5d-encoding region are shown as SEQ ID Nos:13 to 17.

Quick change mutagenesis was performed using the oligonucleotide primers of SEQ ID Nos:18 to 27, and the plasmids pUC19-V29-d1, pUC19-V29-d2, pSL301-V29-d3, pSL301-V29-d4, and pSL301-V29-d5 as templates. As a result, plasmids pUC19-A29-d1, pUC19-A29-d2, pSL301-A29-d3, pSL301-A29-d4, and pSL301-A29-d5 were obtained, each of which contained a DNA fragment encoding C-G29A containing a substitution of Ala for Val-29 of the domain. The five fragments were sequentially ligated to one another with Ligation High. In this manner, an expression plasmid pNK3262-C-G29A.5d containing the DNA fragment (SEQ ID No:29) encoding C-G29A.5d (SEQ ID No:28) was prepared. Then, this plasmid was used for transformation of FY-1 recombinant cells. The quick change mutagenesis was performed in accordance with the protocol of Stratagene using Pfu Turbo DNA polymerase and the methylated DNA (template DNA) cleavage enzyme DpnI (both available from Stratagene). For example, the quick change mutagenesis was performed on the plasmid pUC19-V29-d1 containing the DNA fragment of SEQ ID No: 13 with two synthetic DNA primers of SEQ ID Nos:18 and 19, thereby providing a plasmid pUC19-A29-d1 containing a DNA fragment for the domain 1 containing a substitution of Ala for Val-29.

[Example 2] Preparation of DNAs Encoding C-G29A/S33E.5d, C-G29A/D36R.5d and C-G29A/K35R/D37E.5d The same techniques based on quick change mutagenesis as in Example 1 were applied using the oligonucleotide primers of SEQ ID Nos:30 to 59, and the five plasmids each containing a C-G29A-encoding DNA fragment, pUC19-A29-d1, pUC19-A29-d2, pSL301-A29-d3, pSL301-A29-d4, and pSL301-A29-d5 prepared in Example 1, as templates. As a result, plasmids containing DNA fragments encoding C-G29A/S33E, C-G29A/D36R, and C-G29A/K35R/D37E were prepared.

Subsequently, the DNA fragments were ligated in the manner described in Example 1 so that an expression plasmid pNK3262-C-G29A/S33E.5d containing the DNA fragment (SEQ ID No:61) encoding C-G29A/S33E.5d (SEQ ID No:60), an expression plasmid pNK3262-C-G29A/D36R.5d containing the DNA fragment (SEQ ID No:63) encoding C-G29A/D36R.5d (SEQ ID No:62), and an expression plasmid pNK3262-C-G29A/K35R/D37E. 5d containing the DNA fragment (SEQ ID No:65) encoding C-G29A/K35R/D37E.5d (SEQ ID No:64) were prepared. These plasmids were used for transformation of FY-1 recombinant cells. For ligation of the DNA fragments encoding C-G29A, the restriction enzyme HindIII was used. Since the HindIII recognition sequence was close to the mutation site, a plasmid containing the DNA fragment encoding the unmutated domain 2 and the DNA fragment encoding the mutated domain 3 connected through the HindIII site was prepared, and then the corresponding mutation was introduced in the domain 2-encoding region. Additionally, the DNA fragment (SEQ ID No:69) encoding C-G29A/S33E.4d (SEQ ID No:68) was amplified by PCR using pNK3262-C-G29A/S33E. 5d as a template plasmid and the oligonucleotide primers of SEQ ID Nos:66 and 67. The amplified DNA fragments were digested with PstI and XbaI, and inserted into the vector pNK3262 digested with the same enzymes. In this manner, an expression plasmid pNK3262-C-G29A/S33E.4d was prepared, and used for transformation of FY-1 recombinant cells.

[Example 3] DNA Sequence Determination

The DNA base sequences of the expression plasmids obtained in Examples 1 and 2 were determined using a DNA sequencer 3130x1 Genetic Analyzer (Applied Biosystems). Using BigDye Terminator v. 1. 1 Cycle Sequencing Kit (Applied Biosystems) in accordance with the attached protocol, PCR of these plasmid DNAs for sequencing was carried out, and the sequencing products were purified and sequenced. The sequences of the oligonucleotide primers for sequencing were omitted here.

[Example 4] Expression of Target Protein in Expressing Recombinant Cell

The *Brevibacillus choshinensis* FY-1 recombinant cells obtained in Examples 1 and 2 were cultured with shaking for 3 days at 30° C. in 5 mL of 3YC medium (3% polypeptone, 0.2% yeast extract, 3% glucose, 0.01% magnesium sulfate, 0.001% iron sulfate, 0.001% manganese chloride, 0.0001% zinc chloride) containing 60 μg/mL neomycin.

Each culture was centrifuged to remove cells, and the obtained culture supernatant was subjected to cation exchange chromatography using an SP Fast Flow column (GE Healthcare, Japan) to purify (partially purify) the target protein. Specifically, sodium acetate was added to the culture supernatant to a final concentration of 50 mM, and hydrochloric acid was also added to adjust the pH to 4.0. Then, the culture supernatant was applied to the SP Fast Flow column equilibrated with a cation exchange buffer A (50 mM $CH_3COOH$—$CH_3COONa$, pH 4.0). After washing the column with the cation exchange buffer A, the target protein was eluted and separated in the process of salt gradient elution using the cation exchange buffer A and a cation exchange buffer B (50 mM $CH_3COOH$—$CH_3COONa$, 1 M NaCl, pH 4.0).

Next, the target protein was purified by anion exchange chromatography using a DEAE Fast Flow column (GE Healthcare, Japan). Specifically, the separated target protein solution was dialyzed with ultrapure water, and applied to the DEAE Fast Flow column equilibrated with an anion exchange buffer A (50 mM Tris-HCl, pH 8.0). After washing with the anion exchange buffer A, the target protein was eluted and separated in the process of salt gradient elution using the anion exchange buffer A and an anion exchange buffer B (50 mM Tris-HCl, 0.3 M NaCl, pH 8.0). The separated target protein solution was re-dialyzed with ultrapure water. In this manner, an aqueous solution containing only the target protein was obtained as a final purified sample.

The protein purification processes by chromatography using the columns were carried out using an AKTAprime plus system (GE Healthcare, Japan).

[Example 5] Analysis of Affinity of Obtained Proteins for Human Immunoglobulin G (Human IgG)

The proteins obtained in Example 4 were analyzed for affinity for an immunoglobulin by a biosensor Biacore 3000 (GE health care, Japan) utilizing surface plasmon resonance. In the present example, a human immunoglobulin G drug (hereinafter, referred to as human IgG) separated from human plasma was used. The human IgG was immobilized on a sensor chip, and each protein was added on the chip to detect an interaction between them. The immobilization of the human IgG on the sensor chip CM5 was carried out by amine coupling using N-hydroxysuccinimide (NHS) and N-ethyl-N'-(3-dimethylaminopropyl)carbodiimide hydrochloride (EDC), and ethanolamine was used for blocking (all the sensor chips and the immobilization reagents are available from GE health care, Japan). The human IgG solution was prepared by dissolving Gammagard (Baxter) in a standard buffer (20 mM $NaH_2PO_4$—$Na_2HPO_4$, 150 mM NaCl, pH 7.4) to a concentration of 1.0 mg/mL. The human IgG solution was diluted to 1/100 in an immobilization buffer (10 mM $CH_3COOH$—$CH_3COONa$, pH 4.5) and the human IgG was immobilized on the sensor chip in accordance with the protocol attached to the Biacore 3000. A reference cell to be used as a negative control was also prepared by immobilizing ethanolamine on another flow cell on the chip after activation by EDC/NHS. The protein solutions were appropriately prepared at concentrations of 10 to 1000 nM using a running buffer (20 mM $NaH_2PO_4$—$Na_2HPO_4$, 150 mM NaCl, 0.005% P-20, pH 7.4) (solutions of three different protein concentrations were prepared for each protein), and each protein solution was added on the sensor chip at a flow rate of 20 μL/min for 30 seconds. A sensorgram of the binding reaction at 25° C. was sequentially plotted during the addition (binding phase, 30 seconds) and after the addition (dissociation phase, 60 seconds). After each sensorgram determination, the sensor chip was regenerated by adding 50 mM NaOH (for 15 seconds) (this process was performed to remove the added proteins remaining on the sensor chip and it was confirmed that the binding activity of the immobilized human IgG was substantially completely recovered). The binding rate constant ($k_{on}$), dissociation rate constant ($k_{off}$), affinity constant ($K_A=k_{on}/k_{off}$) and dissociation constant ($K_D=k_{off}/k_{on}$) were calculated by performing a fitting analysis on each of the obtained binding reaction sensorgrams (the binding reaction sensorgrams obtained by subtracting the binding reaction sensorgram of the reference cell) by using the 1:1 binding model in a software BIA evaluation attached to the system.

As shown in Table 1, the binding parameters of the proteins to the human IgG were at similar levels to those of C-G29A.5d (Comparative Example 1). Specifically, the affinity constants (KA) of all the proteins for the human IgG fell in the range of $5.0\times10$ $M^{-1}$ to $5.0\times10^8$ $M^{-1}$.

TABLE 1

| | $K_{on}$ (×$10^5$ $M^{-1}s$) | $K_{off}$ ($10^{-3}$ $s^{-1}$) | $K_A$ (×$10^8$ $M^{-1}$) |
|---|---|---|---|
| C-G29A.5d | 4.1 | 0.88 | 4.7 |
| C-G29A/S33E.5d | 3.0 | 1.3 | 2.3 |
| C-G29A/D36R.5d | 4.6 | 1.5 | 3.0 |
| C-G29A/K35R/D37E.5d | 0.86 | 1.3 | 0.65 |

[Example 6] Preparation of Fab Fragment Derived from Humanized Monoclonal Antibody In the present invention, the "affinity for the Fab region" was analyzed using an Fab fragment free from the Fc region of an immunoglobulin.

The Fab fragment was prepared by fragmenting a humanized monoclonal IgG drug as a starting material into an Fab fragment and an Fc fragment by using papain, and separating and purifying only the Fab fragment.

Specifically, herceptin (humanized monoclonal IgG drug available from Chugai Pharmaceutical Co., Ltd.) was dissolved in a papain digestion buffer (0.1 M AcOH—AcONa, 2 mM EDTA, 1 mM cysteine, pH 5.5). Papain Agarose from papaya latex (papain-immobilized agarose available from SIGMA) was added to the solution, and the resulting mixture was incubated for about 8 hours at 37° C. while being mixed with a rotator. By ion exchange chromatography using a Resource S column (GE health care, Japan), the Fab fragment (hereinafter, referred to as monoclonal IgG-Fab) was separated and purified from the reaction solution (containing both the Fab fragment and the Fc fragment) which had been separated from the papain-immobilized agarose. More specifically, the reaction solution was diluted to pH 4.5 in an ion exchange buffer A (50 mM $CH_3COOH$—$CH_3COONa$, pH 4.5), and then added to the Resource S column equilibrated with the ion exchange buffer A. After washing the column with the ion exchange buffer A, the monoclonal IgG-Fab was eluted and separated in the process of salt gradient elution using the ion exchange buffer A and an ion exchange buffer B (50 mM $CH_3COOH$—$CH_3COONa$, 1 M NaCl, pH 4.5) (the buffer B concentration was linearly increased from 0% to 50% during the process of allowing the buffers in a total amount corresponding to the volume of 10 columns to pass through the column).

The separated monoclonal IgG-Fab solution was purified by gel filtration chromatography using a Superdex 75 10/300 GL column (the standard buffer was used for equilibration and separation). In this manner, a monoclonal IgG-Fab solution was obtained.

The protein purification by chromatography was performed using the AKTAprime plus system in the same manner as in Example 4.

[Example 7] Analysis of Affinity of Obtained Proteins for Monoclonal IgG-Fab

The affinity of the proteins obtained in Example 4 for the IgG-Fab was also analyzed using the Biacore 3000 in the same manner as in Example 5.

The monoclonal IgG-Fab obtained in Example 6 was immobilized on the sensor chip CM5, and each protein obtained in Example 4 was added on the chip to detect an interaction between them. Human serum albumin (Sigma Aldrich) was immobilized on a reference cell. The immobilization of the monoclonal IgG-Fab and the human serum albumin was carried out in the same manner as in Example 5.

Protein solutions of different concentrations (4 µM, 8 µM, 16 µM, 32 µM (32 µM samples of some proteins were not prepared)) were prepared for each of the proteins to be measured, using a running buffer (20 mM $NaH_2PO_4$—$Na_2HPO_4$, 150 mM NaCl, 0.005% P-20, pH 7.4). Each protein solution was added on the sensor chip at a flow rate of 20 µL/min for 30 seconds, and a sensorgram of the binding reaction at 25° C. was sequentially plotted during the addition (binding phase, 30 seconds) and after the addition (dissociation phase, 60 seconds). After each sensorgram determination, 10 mM NaOH was added for 30 seconds for regeneration of the sensor chip. The analysis was conducted in the same manner as in Example 6. It should be noted that $R_{max}$, one of binding parameters, was regarded as a constant in the fitting analysis. The $R_{max}$ is the signal amount obtained when added molecules are bound to all immobilized molecules, and could not largely change in these experiments in which the same molecules (monoclonal IgG-Fab) are immobilized. If the binding signal is very weak, however, a fitting is incorrectly made so that the $R_{max}$ is regarded as an extremely small value. Hence, the $R_{max}$ was regarded as a constant in the fitting. As shown in Table 2, the binding parameters of the proteins to the monoclonal IgG-Fab were significantly lower than those of C-G29A.5d (Comparative Example 1). Specifically, the affinity constants (KA) of all the proteins to the monoclonal IgG-Fab were less than 1/10 of that of C-G29A.5d.

TABLE 2

|  | $k_{on}$ (×$10^4$ $M^{-1}$s) | $k_{off}$ ($s^{-1}$) | $K_A$ (×$10^5$ $M^{-1}$) |
|---|---|---|---|
| C-G29A.5d | 5.8 | 0.13 | 4.4 |
| C-G29A/S33E.5d | 0.056 | 0.40 | 0.014 |
| C-G29A/D36R.5d | 0.22 | 0.39 | 0.057 |
| C-G29A/K35R/D37E.5d | 0.23 | 0.41 | 0.059 |

[Example 8] Preparation of Transformant Cells Capable of Expressing Single-Domain Variants In order to effectively evaluate other mutations disclosed herein in addition to the mutations evaluated in Example 7, single-domain variants were prepared.

The amino acid sequence (SEQ ID No:10, C-G29A.1d) derived from the C domain of Protein A was chosen as a protein sequence to be mutated. A GST fusion protein expression vector pGEX-6P-1 (GE Healthcare, Japan) containing the DNA sequence encoding C-G29A.1d of SEQ ID No:70 was used as a template plasmid for mutation. The template plasmid was prepared in accordance with the description of WO 2010/110288.

Expression plasmids encoding C domain variants (C-G29A/S33L.1d, C-G29A/S33T.1d, C-G29A/D36I.1d, C-G29A/D36R.1d, and C-G29A/D37E.1d) of SEQ ID Nos: 81 to 85 were obtained by quick change mutagenesis using the two plasmids as templates and the oligonucleotide primers of SEQ ID Nos:71 to 80. For example, the C domain variant (C-G29A/S33L.1d) of SEQ ID No:81 was obtained by quick change mutagenesis using the expression plasmid (pGEX-6P-1-C-G29A.1d) containing the DNA sequence of SEQ ID No:70 as a template and the oligonucleotide primers of SEQ ID Nos:71 and 72. The DNA sequences of the obtained expression plasmids were determined in the same manner as in Example 3. The obtained expression plasmids were used for transformation of *E. coli* HB101 (Takara Bio Inc.) in the same manner as in Example 1.

[Example 9] Expression and Purification of Single-Domain Variants

The transformants obtained in Example 8 were capable of expressing the respective variants in the form of GST fusion proteins. Each of these transformants was cultured in LB medium containing ampicillin at 37° C. overnight. Each culture liquid was inoculated in 2xYT medium (containing ampicillin) and cultured at 37° C. for about 1 hour. IPTG (isopropyl-1-thio-β-D-galactoside) was added to a final concentration of 0.1 mM, followed by further culturing at 37° C. for 18 hours. After the culturing, cells were collected by centrifugation and resuspended in PBS buffer containing EDTA (0.5 mM). The cells were sonicated and centrifuged to separate a supernatant fraction (cell-free extract) and an insoluble fraction. The GST fusion proteins were purified (partially purified) from the cell-free extracts containing the GST fusion proteins by affinity chromatography using a GSTrap FF column (GE Healthcare, Japan), which has an affinity for GST. Each cell-free extract was applied to the GSTrap FF column, and the column was washed with a standard buffer (20 mM $NaH_2PO_4$—$Na_2HPO_4$, 150 mM NaCl, pH 7.4). Then, the target GST fusion protein was eluted with an elution buffer (50 mM Tris-HCl, 20 mM glutathione, pH 8.0). The eluted fraction was subjected to exchange with the standard buffer by ultrafiltration. The solutions thus obtained were treated as final purified samples.

[Example 10] Analysis of Affinity of Single-Domain Variants to Monoclonal IgG-Fab The single-domain variants obtained in Example 9 were measured for affinity for the monoclonal IgG-Fab by Biacore in the same manner as in Example 7 to analyze the changes of the binding ability to IgG-Fab caused by the introduced mutations. Here, only sensorgrams of the single-domain variants at a protein concentration of 4 µM (at which the variants had the same absorbance at 280 nm) were determined.

FIG. 2 show the resulting IgG-Fab binding sensorgrams. The proteins showed significantly reduced binding responses to the monoclonal IgG-Fab compared with that of C-G29A.1d (Comparative Example 3) and their responses were reduced to undetectable levels. Thus, the mutations obtained in the present invention were found to reduce the Fab binding ability. Here, since the responses were reduced to undetectable levels, their affinity constants were not calculated.

[Example 11] Evaluation of Alkali Resistance of C-G29A/S33E.5d

C-G29A/S33E.5d obtained in example 4 was evaluated for alkali resistance by comparing decreases in the binding amount to the human IgG (remaining binding activity to the human IgG) before and after incubation under alkaline conditions for a predetermined period.

Specifically, the binding amount of C-G29A/S33E 5d to the human IgG was measured using the Biacore 3000 before and after an alkali treatment. In the alkali treatment, to a 26.2 µM sample of the protein (10 µL) was added a certain amount of 0.625 M NaOH to a final concentration of 0.5 M. The mixture was incubated for 8 hours at 30° C. Subsequently, 0.5 M HCl (in a certain amount that had been confirmed to neutralize the pH) was added to the treated solution to neutralize the solution. The solution was then diluted to ½ in a running buffer (20 mM $NaH_2PO_4$—$Na_2HPO_4$, 150 mM NaCl, 0.005% P-20, pH 7.4). In this manner, a C-G29A/S33E.5d solution after the alkali treatment was prepared.

In order to achieve the same protein concentration and the same solution composition as those of the above solution, a C-G29A/S33E.5d solution before the alkali treatment was prepared by preparing a mixed solution of the NaOH solution used for the alkali treatment and the HCl solution used for the neutralization treatment in advance, and adding the mixed solution to a 26.2 µM sample of C-G29A/S33E.5d (10 µL). Preparation of a sensor chip (e.g. immobilization of the human IgG), the running buffer used for the measurement, the measurement temperature, and the regeneration treatment of the chip were the same as those in Example 7. Each of the C-G29A/S33E.5d solutions before and after the alkali treatment was added on the sensor chip at a flow rate of 20 µL/min for 150 seconds. A binding reaction sensorgram was then sequentially plotted during the addition (binding phase, 150 seconds) and after the addition (dissociation phase, 210 seconds).

The analysis was conducted in the same manner as in Example 5. Here, an additional interpretation of the obtained binding parameters is provided. In this analysis, the protein concentrations of the solutions before and after the alkali treatment were the same, but the concentrations of the protein having binding activity to the human IgG were different from each other. However, since fitting using the concentration as a variable is difficult, each concentration was considered to be the same before and after the treatment in the fitting analysis. In this case, the concentration difference of the protein having binding activity to IgG is reflected on the parameter $R_{max}$, which is the maximum binding capacity. Therefore, the alkali resistance of C-G29A/S33E.5d was evaluated by calculating and comparing the relative value of the $R_{max}$ after the alkali treatment to the $R_{max}$ before the alkali treatment (remaining IgG binding activity (%)).

C-G29A.5d (Comparative Example 1) had a remaining IgG binding activity after the alkali treatment of 85.4%, whereas C-G29A/S33E.5d had a remaining IgG binding activity after the alkali treatment of 85.5%. The results demonstrate that the mutation in the present invention can produce the effect without sacrificing excellent alkali resistance of C-G29A.

[Example 12] Preparation of Affinity Separation Matrices with Obtained Proteins (Ligands) Immobilized thereon Affinity Separation Matrix (1): Methacrylate Polymer-Based As a water-insoluble base material, a commercial activated filler for affinity chromatography "TOYOPEARL AF-Formyl-650M" (Tosoh Corporation) was used. This filler was a methacrylate polymer-based filler already bearing formyl groups for immobilization of a proteinic ligand. The final purified sample of C-G29A/S33E. 5d obtained in Example 4 was used as a ligand and immobilized to prepare affinity separation matrix (1).

More specifically, 5 mL of the filler was subjected to exchange with a citric acid buffer (0.25 M trisodium citrate dihydrate, pH 9.0 adjusted with NaOH) on a glass filter, and the volume was increased to 7.5 mL in total in a centrifuge tube. To this was added 0.64 mL of the C-G29A/S33E.5d-containing solution (64.6 mg/mL), and the resulting mixture was shaken with a mix rotor (MIX ROTOR MR-3 1-336-05 available from AZONE) at 6° C. for 4 hours. Subsequently, the mixture was adjusted to pH 3 with a 2.4 M citric acid aqueous solution and continuously shaken at 6° C. for 4 hours. Then, 2.8 mL of a 5.5% by weight dimethylamine borane aqueous solution (Wako Pure Chemical Industries, Ltd.) was added thereto, and the resulting mixture was shaken at 25° C. for 18 hours. The thus prepared carrier was washed on a glass filter with RO water until the electric conductivity of the washing filtrate fell to 5 µS/cm or less. In this manner, the affinity separation matrix was prepared.

Affinity Separation Matrix (2): Cross-Linked Agarose-Based

As a water-insoluble base material, a commercial 1-mL prepacked activated column "Hitrap NHS activated HP" (GE Healthcare, Japan) was used. This column was a cross-linked agarose-based column already bearing N-hydroxysuccinimide (NHS) groups for immobilization of a proteinic ligand. The final purified sample of C-G29A/S33E.4d obtained in Example 4 was used as a ligand and immobilized in accordance generally with the product manual to prepare affinity separation matrix (2).

More specifically, the final purified sample was diluted to a final concentration of about 6 mg/mL in a coupling buffer (0.2 M sodium carbonate, 0.5 M NaCl, pH 8.3) to prepare a sample diluted solution (1 mL). The procedure of allowing 2 mL of 1 mM HCl cooled in an ice bath to flow through the column at a flow rate of 1 mL/min was carried out three times to remove isopropanol in the column. Then, 1 mL of the sample diluted solution prepared above was immediately added at the same flow rate. The top and bottom of the column were sealed, and the column was then left at rest at 25° C. for 30 minutes. In this manner, the obtained protein was immobilized on the column. Thereafter, the column was opened, and 3 mL of the coupling buffer was allowed to flow therethrough at the same flow rate to recover unreacted protein. Next, the procedure of allowing 2 mL of a blocking buffer (0.5 M ethanolamine, 0.5 M NaCl, pH 8.3) to flow through the column was carried out three times, and the procedure of allowing 2 mL of a washing buffer (0.1 M acetic acid, 0.5 M NaCl, pH 4.0) to flow therethrough was also carried out three times. Finally, 2 mL of a standard buffer (20 mM $NaH_2PO_4$—$Na_2HPO_4$, 150 mM NaCl, pH 7.4) was allowed to flow therethrough. Thus, the preparation of the affinity separation column was completed.

Affinity Separation Matrix (3): Cellulose-Based

As a water-insoluble base material, a commercial gel-filtration filler "Cellulofine GCL-2000-m" (Chisso Corporation) was used. This filler was a cross-linked porous cellulose-based filler. The final purified sample of C-G29A/S33E.5d obtained in Example 4 was used as a ligand and immobilized to prepare affinity separation matrix (3).

More specifically, 12 mL of the filler was subjected to exchange with a citric acid buffer (0.01 M trisodium citrate dihydrate-citric acid monohydrate, pH 3) on a glass filter (17G-2 available from TOP), and the fluid volume was increased to 18 mL in a centrifuge tube. To this was added 6 ml of an aqueous solution containing 0.08 g of sodium periodate (Wako Pure Chemical Industries, Ltd.) dissolved in RO water, and the resulting mixture was shaken with a mix rotor (MIX ROTOR MR-3 1-336-05 from AZONE) at 6° C. for about 30 minutes. The thus prepared product was washed on a glass filter with a sufficient amount of RO water, thereby providing a carrier bearing formyl groups.

Then, 5 mL of the formyl group-bearing carrier was subjected to exchange with a citric acid buffer (0.25 M trisodium citrate dihydrate, pH 8.0 adjusted with NaOH) on a glass filter, and the volume was increased to 8.5 mL in total in a centrifuge tube. To this was added 0.64 mL of the C-G29A/S33E.5d-containing solution (64.6 mg/mL), and the mixture was adjusted to pH 12 with 0.4 M NaOH and then shaken with the mix rotor at 6° C. for 4 hours. Subsequently, the resulting mixture was adjusted to pH 3 with a 2.4 M citric acid aqueous solution (citric acid monohydrate) and then continuously shaken at 6° C. for 4 hours. Subsequently, 2.8 mL of a 5.5% by weight dimethylamine borane aqueous solution was added thereto, and the resulting mixture was shaken at 25° C. for 18 hours. The thus prepared carrier was washed on a glass filter with RO water until the electric conductivity of the washing filtrate fell to 5 µS/cm or less. In this manner, the affinity separation matrix was prepared.

Affinity Separation Matrix (4): Cellulose-Based 2

As a water-insoluble base material, crystalline highly cross-linked cellulose (gel available from Chisso Corporation, disclosed in U.S. Pat. No. 0,062,118 (JP 2009-242770 A)) was used. The final purified sample of C-G29A/S33E.5d obtained in Example 4 was used as a ligand and immobilized to prepare affinity separation matrix (4).

More specifically, 12 mL of the gel was subjected to exchange with a citric acid buffer (0.01 M trisodium citrate dihydrate-citric acid monohydrate, pH 3) on a glass filter, and the fluid volume was increased to 18 mL in a centrifuge tube. To this was added 6 ml of an aqueous solution containing 0.08 g of sodium periodate dissolved in RO water, and the resulting mixture was shaken with the mix rotor at 6° C. for about 30 minutes.

Then, 5 mL of this formyl group-bearing carrier was subjected to exchange with a citric acid buffer (0.25 M trisodium citrate dihydrate, pH 8.0 adjusted with NaOH) on a glass filter, and the volume was increased to 8.5 mL in total in a centrifuge tube. To this was added 0.96 mL of the C-G29A/S33E.5d-containing solution (64.6 mg/mL) obtained in Example 4, and the mixture was adjusted to pH 12 with 0.4 M NaOH and then shaken with the mix rotor at 6° C. for 4 hours. Subsequently, the resulting mixture was adjusted to pH 5 with a 2.4 M citric acid aqueous solution (citric acid monohydrate) and then continuously shaken at 6° C. for 4 hours.

Subsequently, 0.46 mL of a 5.5% by weight dimethylamine borane aqueous solution was added thereto, and the resulting mixture was shaken at 25° C. for 18 hours. After the reaction, the reaction solution was measured for absorbance at the absorption maximum around 275 nm. The result revealed that the amount of C-G29A/S33E.5d introduced was 11 mg/mL-gel, and the yield of the ligand immobilized on the carrier was 90%.

This carrier was washed on a glass filter with RO water until the electric conductivity of the washing filtrate fell to 5 µS/cm or less. Then, the carrier was further washed with a 0.1 M citric acid aqueous solution (citric acid monohydrate), a sodium hydroxide/sodium sulfate mixture aqueous solution (0.05 M NaOH, 0.5 M sodium sulfate), and a citric acid buffer (0.5 M trisodium citrate dihydrate-citric acid monohydrate, pH 6) in this order. Finally, the carrier was washed with RO water until the electric conductivity of the washing filtrate fell to 5 µS/cm or less. In this manner, the affinity separation matrix was prepared.

Figure 3:
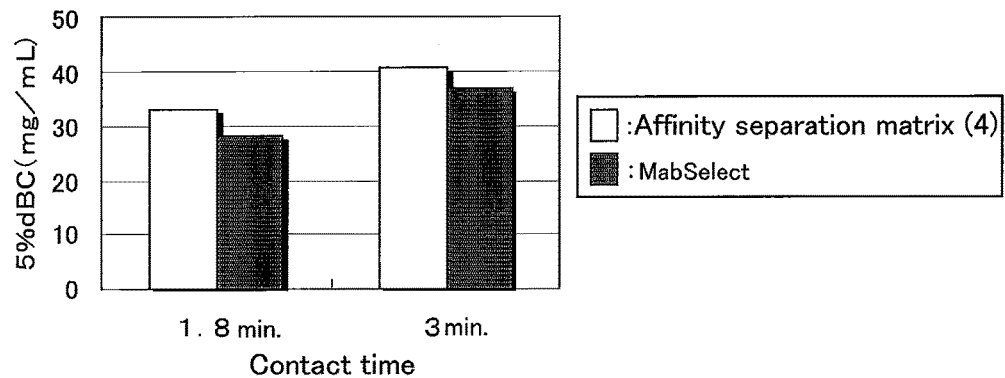
FIG. 3 is a graph of 5% dBCs of the affinity separation matrix (4) of Example 12 of the present invention for an antibody.

This affinity separation matrix (4) was measured in accordance with the method described in WO 2010/064437 to determine the adsorption capacity for an antibody and the amount of ligand leakage. The 5% dBC values at contact times of 1.8 minutes and 3 minutes were 33 and 41 mg/mL, respectively, and the amount of ligand leakage was 30 ppm relative to eluted IgG. Here, the corresponding 5% dBC values of a commercial highly cross-linked agarose carrier "MabSelect" (GE Healthcare Bioscience) measured under the same conditions were 28 and 37 mg/mL, respectively. FIG. 3 shows a graph for comparing the 5% dBC values. The amounts of ligand leakage of commercial affinity separation matrices have been reported in a known literature (Hahn R. et al., "J. Chromatogr. A.", 2006, vol. 1102, pp. 224-231). As described above, the affinity separation matrix (4) obtained in this example was found to have performance parameters important for antibody drug purification at levels sufficient for practical use.

[Example 13] Evaluation of Antibody Elution Properties of Affinity Separation Matrices with Acid An empty column Tricorn™ 5/50 Column (GE Healthcare, Japan) was filled with each of the affinity separation matrices (1) to (4) prepared in Example 12, and the column was connected to a chromato system AKTA prime plus (GE Healthcare, Japan) to evaluate the antibody elution properties in the acidic condition by antibody purification chromatography. Here, the affinity separation matrix (2), which was a prepacked column, could be connected as it was. All the columns had a volume of about 1 mL. After equilibration of each affinity separation column with a standard buffer (20 mM $NaH_2PO_4$—$Na_2HPO_4$, 150 mM NaCl, pH 7.4), 500 µL of a 1 mg/mL solution of herceptin (humanized monoclonal IgG drug of the VH3 subfamily) in the standard buffer was added thereto at a flow rate of 2 mL/min. Subsequently, the column was washed with 5 mL of the standard buffer flowing at the same flow rate, and then 5 mL of an elution buffer (35 mM $CH_3COOH$—$CH_3COONa$, pH 3.5) was also allowed to flow therethrough at the same flow rate. During this period, the absorbance at 280 nm was monitored to determine a chromatographic profile of an IgG elution peak. Continuously, 5 mL of the standard buffer was allowed to flow therethrough at the same flow rate, and then 3 mL of a strong washing solution (0.5 M $CH_3COOH$, 0.1 M $Na_2SO_4$, pH 2.5) was also allowed to flow at the same flow rate. During this period, the absorbance at 280 nm was monitored to determine a peak of forcibly separated IgG which had been still present in the column. Here, only for the affinity separation matrix (2), a strong washing solution (20 mM CH₃COONa—CH₃COOH, 1M NaCl (pH 3.2)) was used.

The affinity separation matrices (1) to (3) were evaluated for antibody elution properties in the acidic condition by carrying out antibody purification chromatography with an elution buffer adjusted to pH 3.75 in the same manner as described above.

Antibody Elution Properties with Acid of Affinity Separation Matrix (1)

Figure 4:
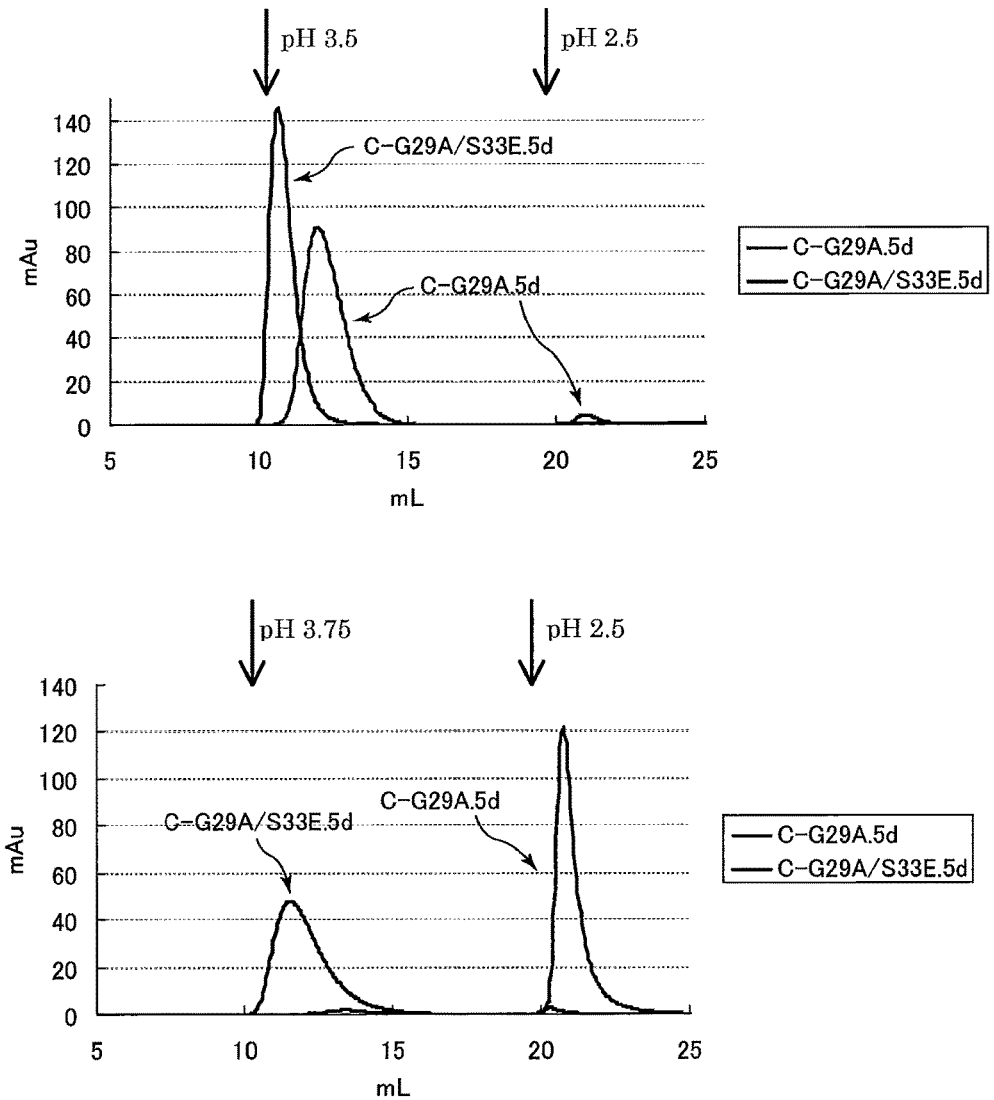
FIG. 4 show elution peak profiles obtained by antibody purification chromatography using the affinity separation matrix (1) in Example 13 of the present invention and Comparative Example 1.

FIG. 4 show graphs on which elution peak profiles obtained by antibody purification chromatography using the affinity separation matrix (1) with C-G29A/S33E.5d or with C-G29A.5d (Comparative Example 1) immobilized instead are superimposed. The upper graph shows elution peak profiles obtained at an elution pH of 3.5, and the lower graph shows elution peak profiles obtained at an elution pH of 3.75. As shown in FIG. 4, the elution peak profiles obtained using the matrix with C-G29A/S33E.5d immobilized thereon were apparently sharper than those obtained using the matrix with C-G29A.5d immobilized thereon. From the elution peak profiles at an elution pH of 3.75, it was demonstrated that recovery of IgG adsorbed on C-G29A.5d, which corresponds to a protein before introduction of the mutation, was difficult but IgG adsorbed on C-G29A/S33E.5d, which corresponds to a protein after introduction of the mutation, could be all recovered. This may be one example showing that the present invention can drastically enhance the antibody recovery rate in the presence of an acidic solution closer to neutral.

Antibody Elution Properties of Affinity Separation Matrix (2) with Acid

Figure 5:
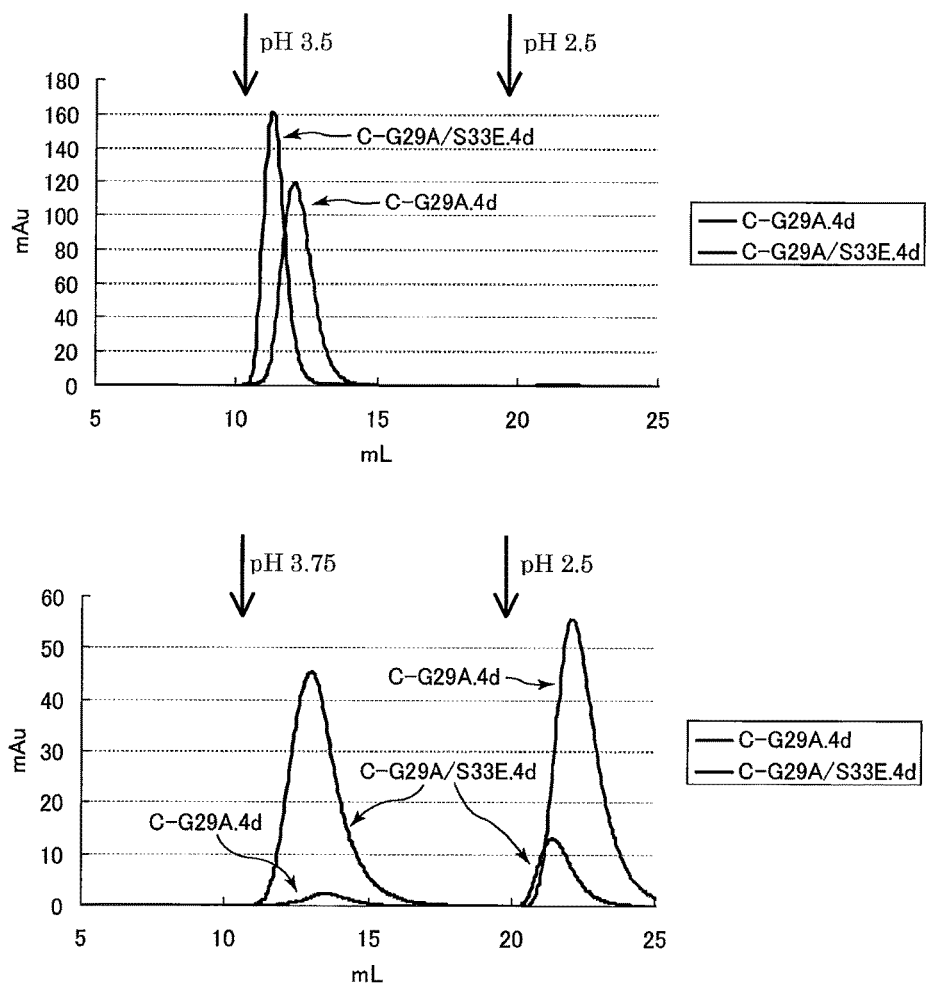
FIG. 5 show elution peak profiles obtained by antibody purification chromatography using the affinity separation matrix (2) in Example 13 of the present invention and Comparative Example 2.

FIG. 5 show graphs on which elution peak profiles obtained by antibody purification chromatography using the affinity separation matrix (2) with C-G29A/S33E.4d or with C-G29A.4d (Comparative Example 2) immobilized instead are superimposed. Likewise, as seen in the case of the affinity separation matrix (1), the elution peak profiles obtained using the matrix with C-G29A/S33E.4d immobilized thereon were apparently sharper than those obtained using the matrix with C-G29A. 4d immobilized thereon. The obtained data demonstrated that the protein of the present invention can produce the effect regardless of the type of the base of the water-insoluble base material, the immobilization method of the ligand on the base material, and the number of domains of the protein serving as a ligand.

Antibody Elution Properties of Affinity Separation Matrix (3) with Acid

Figure 6:
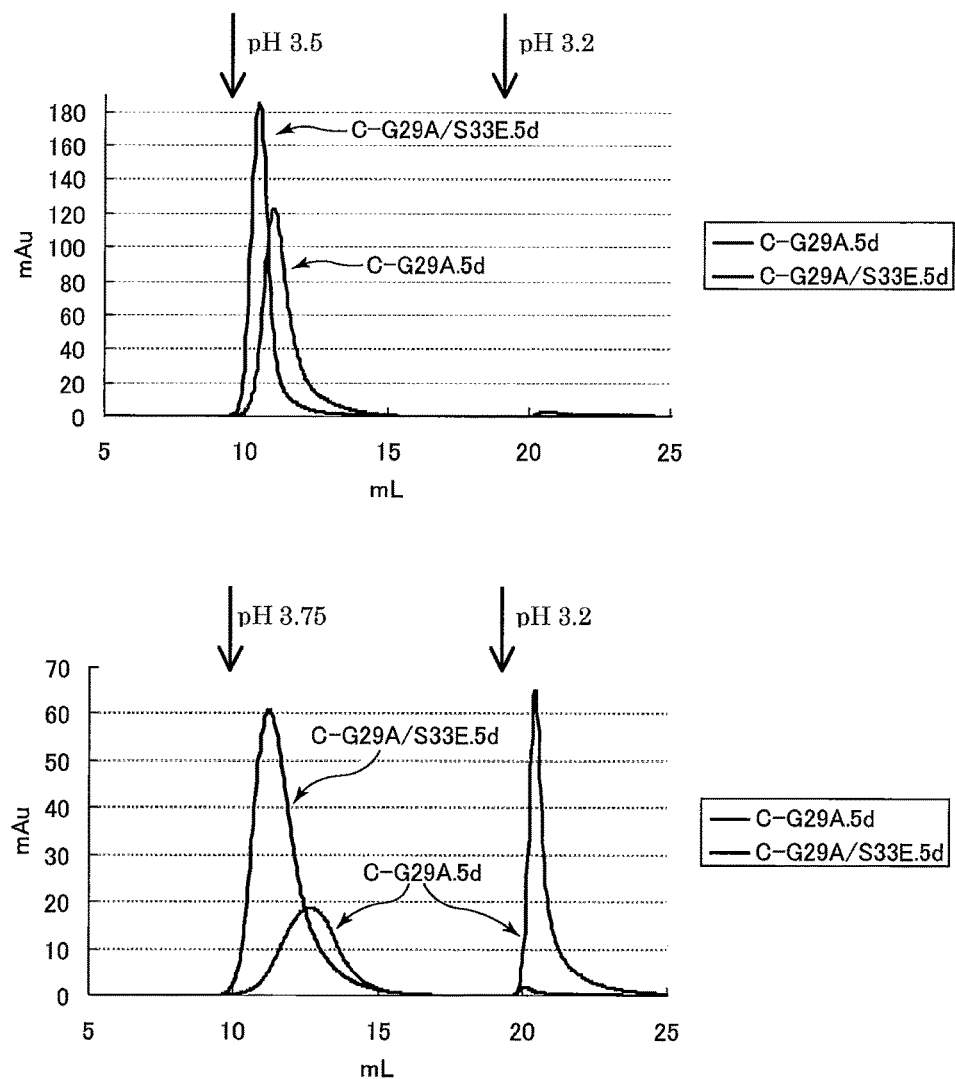
FIG. 6 show elution peak profiles obtained by antibody purification chromatography using the affinity separation matrix (3) in Example 13 of the present invention and Comparative Example 1.

FIG. 6 show graphs on which elution peak profiles obtained by antibody purification chromatography using the affinity separation matrix (3) with C-G29A/S33E.5d or with C-G29A.5d (Comparative Example 1) immobilized instead are superimposed. It was shown that the elution peak profiles obtained using the matrix with C-G29A/S33E.5d immobilized thereon were apparently sharper than those obtained using the matrix with C-G29A.5d immobilized thereon. The obtained data demonstrated that the protein of the present invention can produce a better effect when a base material with excellent antibody elution properties (sharp elution) is used in combination.

Antibody Elution Properties of Affinity Separation Matrix (4) with Acid

Figure 7:
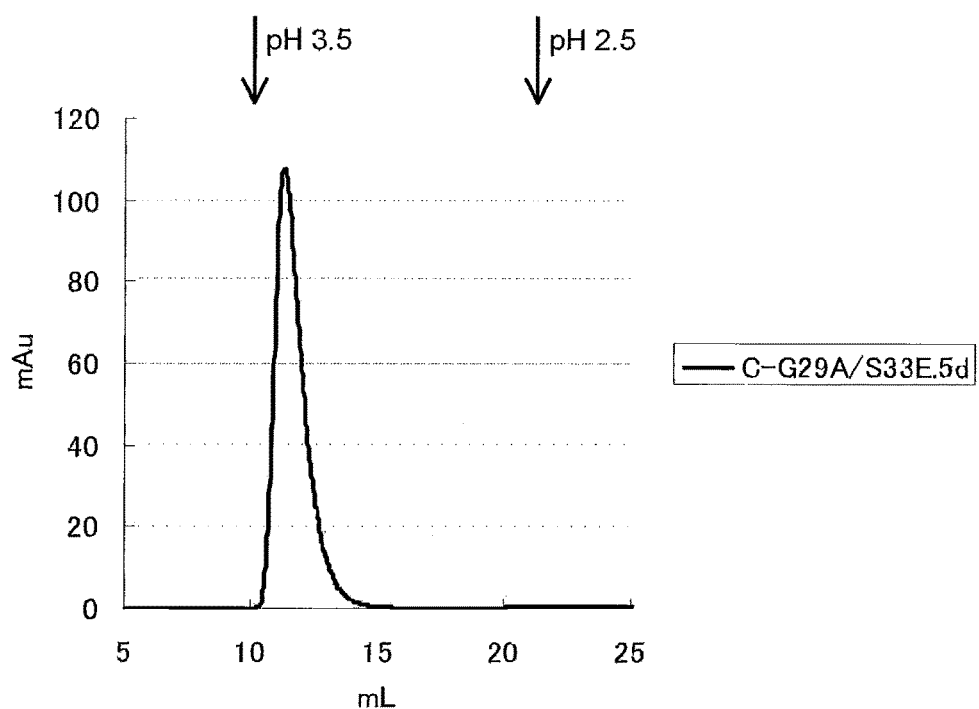
FIG. 7 shows an elation peak profile obtained by antibody purification chromatography using the affinity separation matrix (4) in Example 13 of the present invention.

FIG. 7 shows an elution peak profile (elution pH: 3.5) obtained by antibody purification chromatography using the affinity separation matrix (4) with C-G29A/S33E.5d immobilized thereon. From an industrial point of view, a need for matrices having a high antibody-binding capacity is large. Increase in the amount of immobilized ligands is effective to increase the antibody-binding capacity. The obtained data demonstrated that the present invention can produce the effect without causing any problems even when the amount of immobilized proteins is high.

Comparative Example 1

Preparation and Use of C-G29A.5d

C-G29A.5d (SEQ ID No:28) was prepared using the recombinant cells obtained in Example 1 in the same manner as in Examples 3 to 5. The affinities for the human IgG and the monoclonal IgG-Fab were analyzed in the same manner as in Examples 5 and 7, and the analysis results are also shown in Tables 1 and 2.

The alkali resistance was also evaluated in the same manner as in Example 11. Additionally, C-G29A.5d was used instead for preparation of the affinity separation matrices (1) and (3) in Example 12, and the resulting matrices were evaluated for antibody elution properties in the acidic condition in the same manner as in Example 13. The results are also shown in FIGS. 4 and 6. Here, the solutions used for preparation of the affinity separation matrices (1) and (3) had a protein concentration of 58.2 mg/mL, and the used amount was 0.79 mL.

Comparative Example 2

Preparation and Use of C-G29A.4d

An expression plasmid for C-G29A.4d and transformant cells obtained using the plasmid were prepared using the expression plasmid pNK3262-C-G29A.5d obtained in Example 1 as a template and the oligonucleotide primers of SEQ ID Nos: 66 and 67 in the same manner as in Example 2. C-G29A.4d was prepared in the same manner as in Examples 3 to 5. Additionally, C-G29A.4d was used instead for preparation of the affinity separation matrix (2) in Example 12, and the resulting matrix was evaluated for antibody elution properties in the acidic condition in the same manner as in Example 13. The results are also shown in FIG. 5.

Comparative Example 3

Preparation of C-G29A.1d

C-G29A.1d was prepared using the transformant cells (HB101) containing the template plasmid used in Example 8 in the same manner as in Example 9, and the affinity for the monoclonal IgG-Fab was analyzed in the same manner as in Example 10. The analysis results are also shown in FIG. 2.

The invention claimed is:

1. A protein having an affinity for an immunoglobulin, comprising the amino acid sequence having substitutions and a sequence identity of not less than 90% to the amino acid sequence of SEQ ID NO:5, wherein the amino acid residue corresponding to position 29 of SEQ ID NO:5 is Ala, wherein the amino acid residue corresponding to position 33 of SEQ ID NO:5 is Glu, and/or the amino acid residue corresponding to position 36 of SEQ ID NO:5 is Arg, and wherein the protein has a lower affinity for an Fab region of an immunoglobulin than the protein before introduction of the substitutions.

2. A multi-domain protein, comprising two or more proteins according to claim 1, connected together.

3. The multi-domain protein according to claim 2, wherein the proteins connected together are different from one another.

4. The multi-domain protein according to claim 2, wherein the number of the proteins connected together is 2 to 5.

5. An affinity separation matrix, comprising:
the protein according to claim 1 as an affinity ligand, and a carrier made of a water-insoluble base material on which the protein is immobilized.

6. The affinity separation matrix according to claim 5, wherein the water-insoluble base material comprises a synthetic polymer or a polysaccharide.

7. The affinity separation matrix according to claim 6, wherein the polysaccharide is cellulose.

8. An affinity separation matrix, comprising the protein according to claim 1 as an affinity ligand, and a carrier made of a water-insoluble base material on which the protein is immobilized, wherein the affinity separation matrix binds to a protein containing an Fc region of an immunoglobulin.

9. The affinity separation matrix according to claim 8, wherein the protein containing an Fc region of an immunoglobulin is an immunoglobulin G or an immunoglobulin G derivative,
wherein the immunoglobulin G derivative is at least one member selected from the group consisting of chimeric immunoglobulin Gs, humanized immunoglobulin Gs, and immunoglobulin G whose Fc region has a modified sugar chain and which has a function as an immunoglobulin G and is bound by Protein A.

10. A protein having an affinity for an immunoglobulin, comprising an amino acid sequence having substitutions and a sequence identity of not less than 90% to the amino acid sequence of SEQ ID NO:5, wherein the amino acid residue corresponding to position 29 of SEQ ID NO:5 is Ala, wherein the amino acid residue corresponding to position 33 of SEQ ID NO:5 is Glu or Thr, and/or the amino acid residue corresponding to position 36 of SEQ ID NO:5 is Arg or Ile, and wherein the protein has a lower affinity for an Fab region of an immunoglobulin than the protein before introduction of the substitutions.

11. A DNA encoding the protein according to claim 1.

12. A vector comprising the DNA according to claim 11.

13. A transformant which is obtainable by transformation of a host with the vector according to claim 12.

14. The transformant according to claim 13,
wherein the host is a gram-positive bacterium.

15. The transformant according to claim 14,
wherein the gram-positive bacterium is a bacterium of *Brevibacillus*.

16. The transformant according to claim 15,
wherein the bacterium of *Brevibacillus* is *Brevibacillus choshinensis*.

17. A method for producing the protein according to claim 1, the method comprising utilizing a transformant which is obtainable by transformation of a host with a vector comprising a DNA encoding the protein, or a cell-free protein synthesis system using a DNA encoding the protein.

18. The production method according to claim 17, comprising:
accumulating the protein intracellularly and/or in a periplasmic space of the transformant; and/or
secreting the protein extracellularly from the transformant.

* * * * *